United States Patent
Basu et al.

(10) Patent No.: US 9,266,889 B2
(45) Date of Patent: Feb. 23, 2016

(54) COMPOSITION, SYNTHESIS, AND USE OF NEW SUBSTITUTED PYRAN AND PTERIN COMPOUNDS

(71) Applicant: DUQUESNE UNIVERSITY OF THE HOLY GHOST, Pittsburgh, PA (US)

(72) Inventors: Partha Basu, Pittsburgh, PA (US); Igor Pimkov, Pittsburgh, PA (US)

(73) Assignee: Duquesne University of the Holy Ghost, Pittsburgh, PA (US)

( * ) Notice: Subject to any disclaimer, the term of this patent is extended or adjusted under 35 U.S.C. 154(b) by 0 days.

(21) Appl. No.: 14/581,314

(22) Filed: Dec. 23, 2014

(65) Prior Publication Data

US 2015/0203497 A1    Jul. 23, 2015

Related U.S. Application Data

(62) Division of application No. 13/735,511, filed on Jan. 7, 2013, now Pat. No. 8,946,450, which is a division of application No. 13/072,092, filed on Mar. 25, 2011, now Pat. No. 8,378,123.

(51) Int. Cl.
| | |
|---|---|
| C07D 475/04 | (2006.01) |
| C07D 495/04 | (2006.01) |
| C07D 409/04 | (2006.01) |
| C07D 487/04 | (2006.01) |
| C07D 495/14 | (2006.01) |

(52) U.S. Cl.
CPC ............ *C07D 475/04* (2013.01); *C07D 409/04* (2013.01); *C07D 487/04* (2013.01); *C07D 495/04* (2013.01); *C07D 495/14* (2013.01)

(58) Field of Classification Search
CPC ... C07D 409/04; C07D 475/04; C07D 495/04
See application file for complete search history.

(56) References Cited

U.S. PATENT DOCUMENTS

| | | | |
|---|---|---|---|
| 6,518,335 B2 | 2/2003 | Reedy et al. | |
| 7,504,095 B2 | 3/2009 | Schwarz et al. | |
| 2008/0182337 A1* | 7/2008 | Basu .................... | C07D 495/14 436/172 |
| 2010/0041158 A1* | 2/2010 | Basu .................... | C07D 495/14 436/73 |

OTHER PUBLICATIONS

Hammerschmidt, F. et al., "The Phosphonate-Phosphate and Phosphate-Phosphonate Rearrangement and Their Applications V [1]. On the Reaction of s-Butyllithium/TMEDA with Symmetrical Trialkyl Phosphates", Monatschefte fur Chemie 128, 1173-1180 (1997), Austria.
Dorwald, F, Zaragonza, Side Reactions in Organic Synthesis: A Guide to Successful Synthesis Design, Weinheim: Wiley-VCH Verlag GmbH & Co., KGaA, 2005, Preface.

* cited by examiner

*Primary Examiner* — Valerie Rodriguez-Garcia
(74) *Attorney, Agent, or Firm* — Eckert Seamans Cherin & Mellott, LLC; Carol A. Marmo

(57) ABSTRACT

The present invention relates to substituted pterin compounds, their synthesis and use. In particular, the present invention relates to a new precursor compound and its analogs for synthesizing a new substituted pterin compound and its analogs. These new compounds are particularly suitable for treating molybdenum cofactor deficiency.

4 Claims, 38 Drawing Sheets

High resolution mass spectrum (ESI+) of compound 14 and 15.

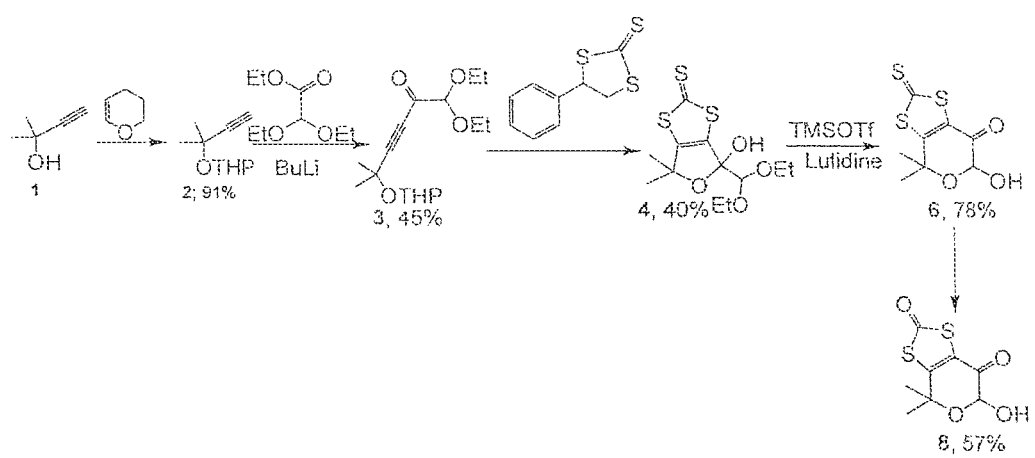
Figure 1. Representation of a synthetic scheme for pyran dithiolene complexes.

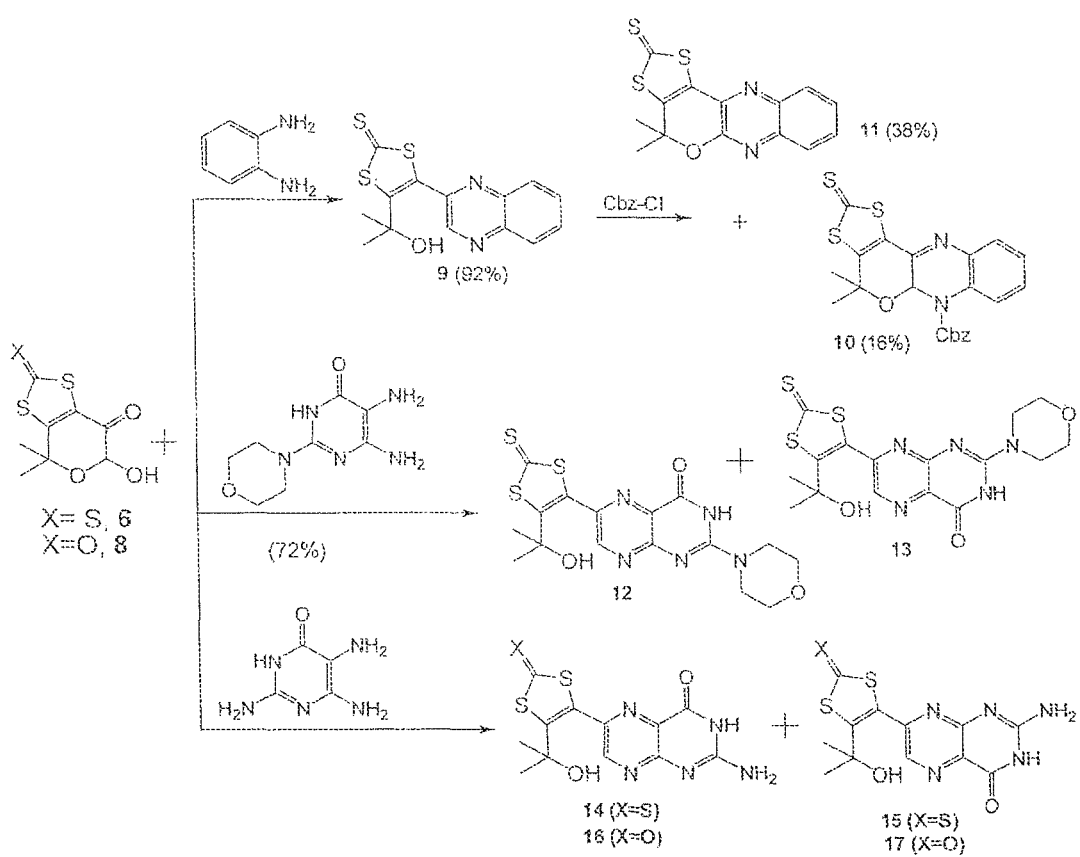
Figure 2. Representation of a synthetic scheme for pterin and quinoxaline dithiolene complexes.

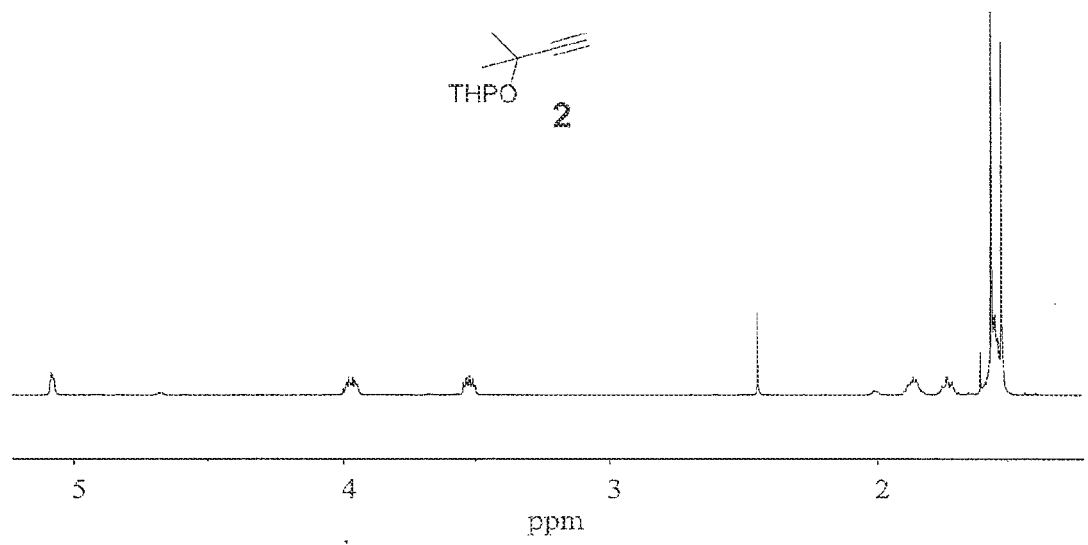
Figure 3. $^1$H NMR spectrum of compound 2 in CDCl$_3$.

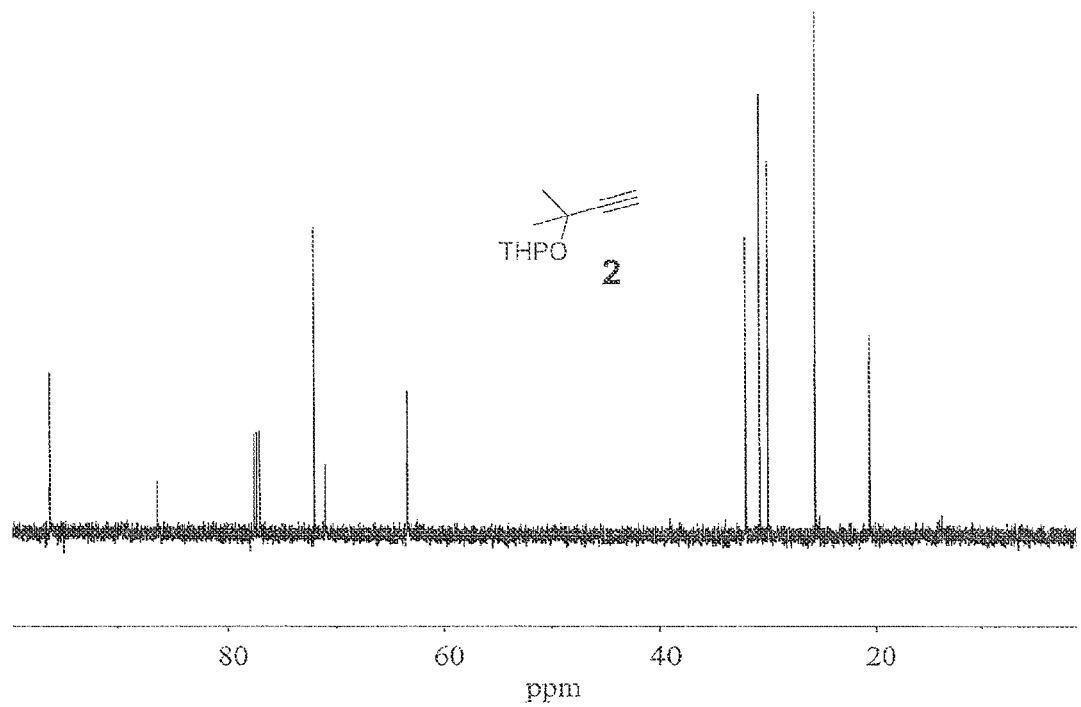
Figure 4. $^{13}$C NMR spectrum of compound 2 in CDCl$_3$.

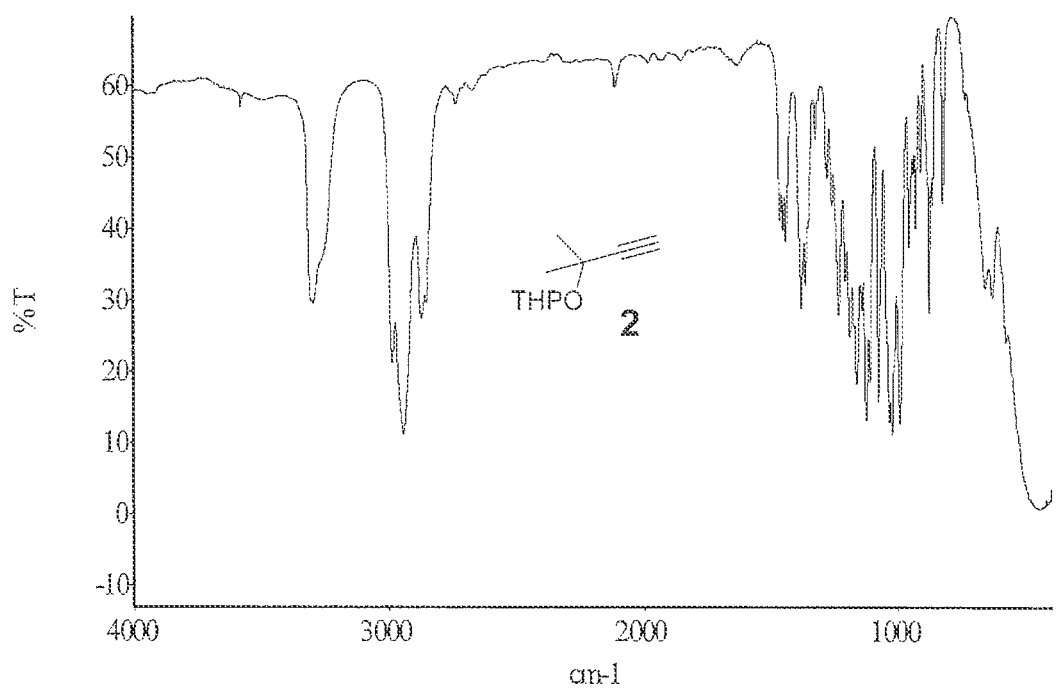
Figure 5. Infrared spectrum (neat) of compound 2.

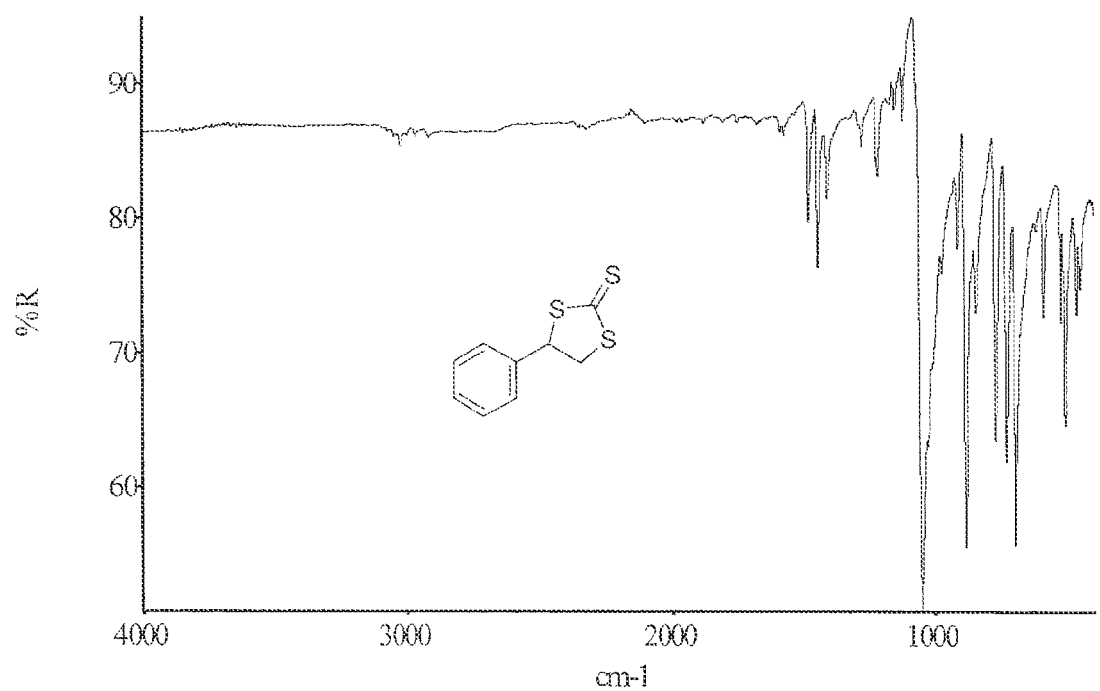
Figure 6. Infrared spectrum (neat) of 4-phenyl-1,3-dithiolane-2-thione.

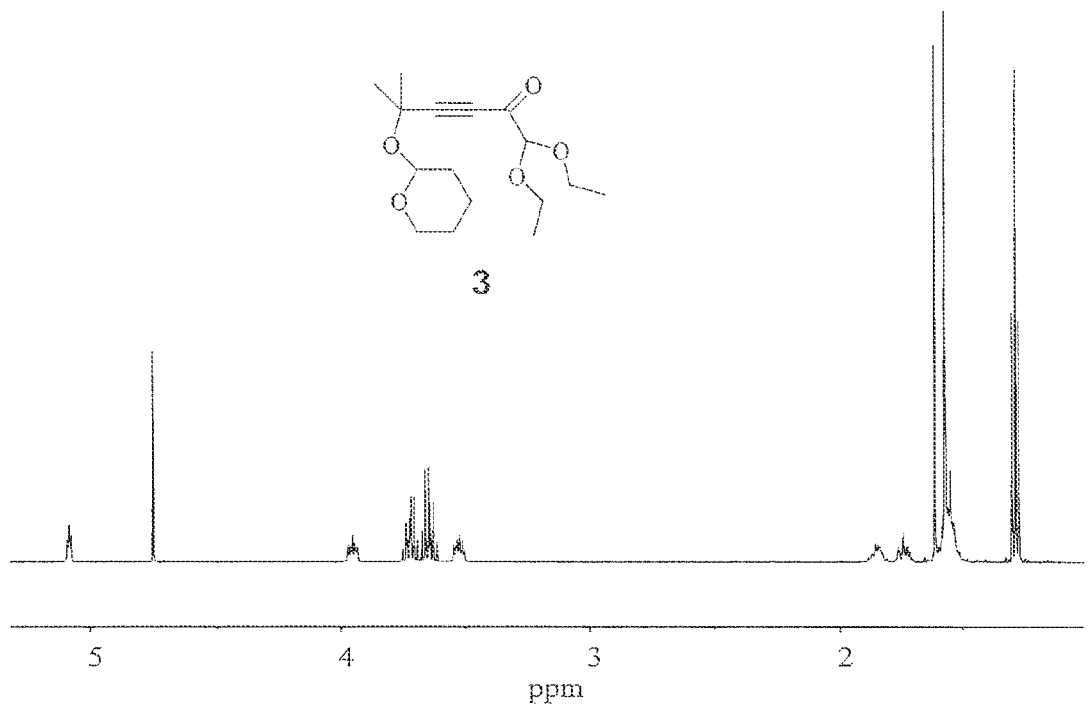
Figure 7. ¹H NMR spectrum of compound 3 in CDCl₃

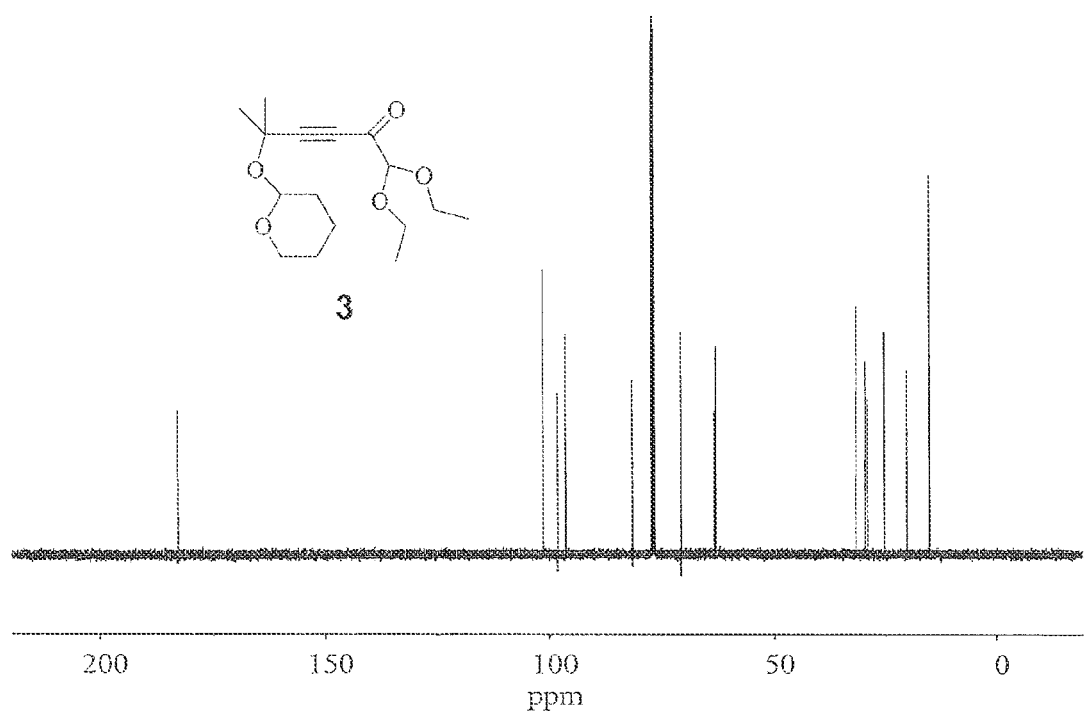
Figure 8. $^{13}$C NMR spectrum of compound 3 in CDCl$_3$.

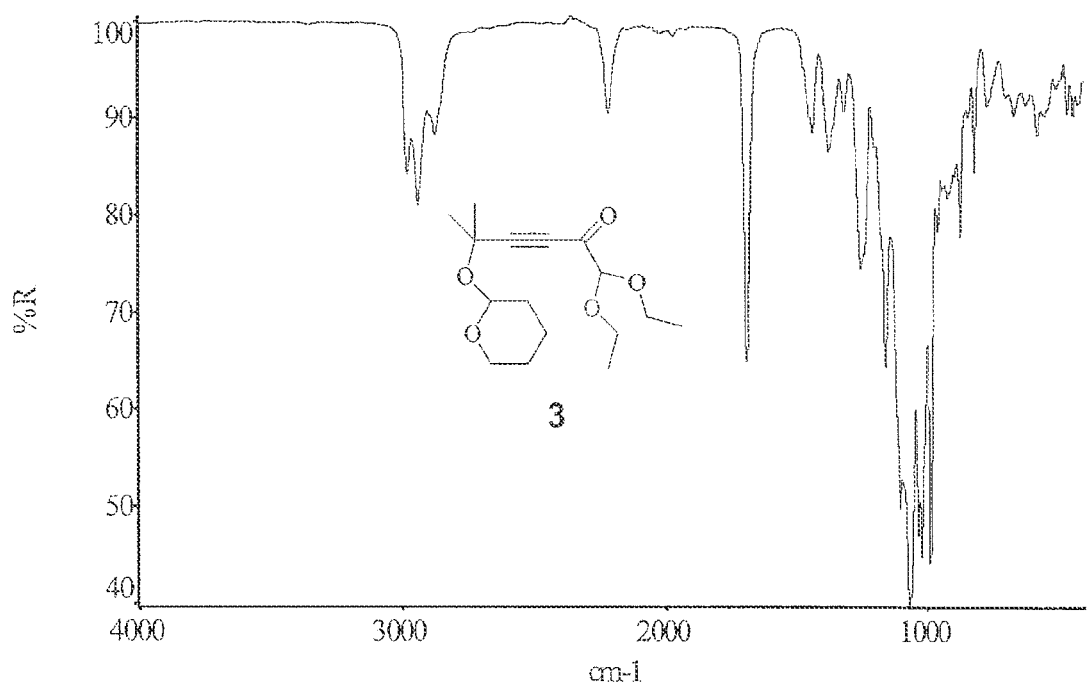
Figure 9. Infrared spectrum (neat) of compound 3.

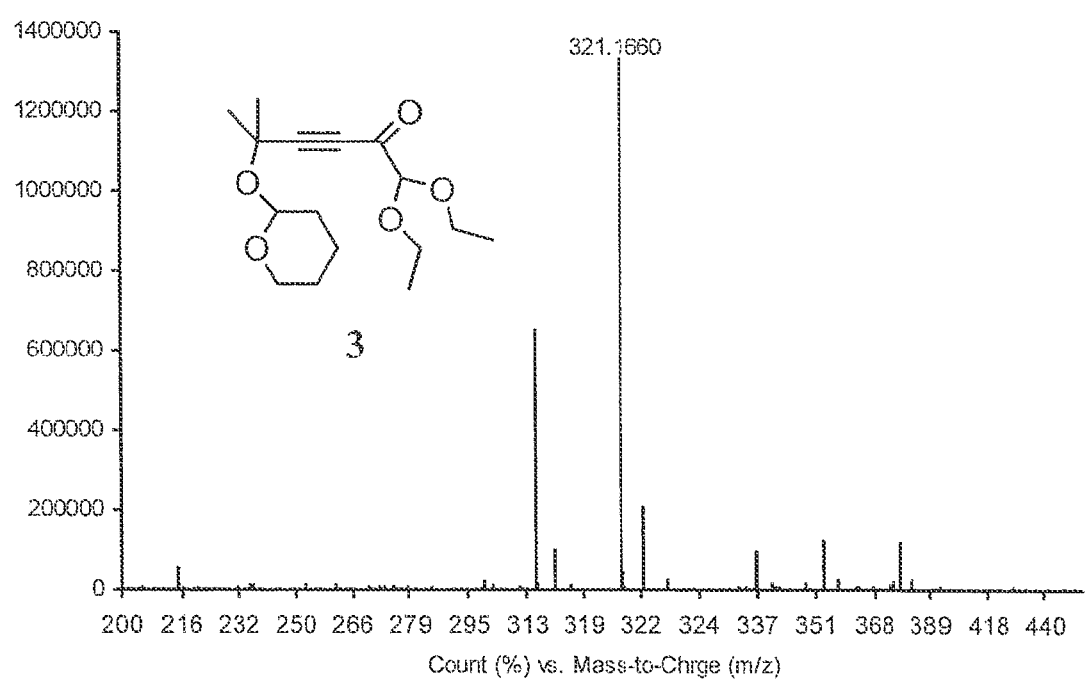
Figure 10. High resolution mass spectrum (ESI⁺) of compound 3.

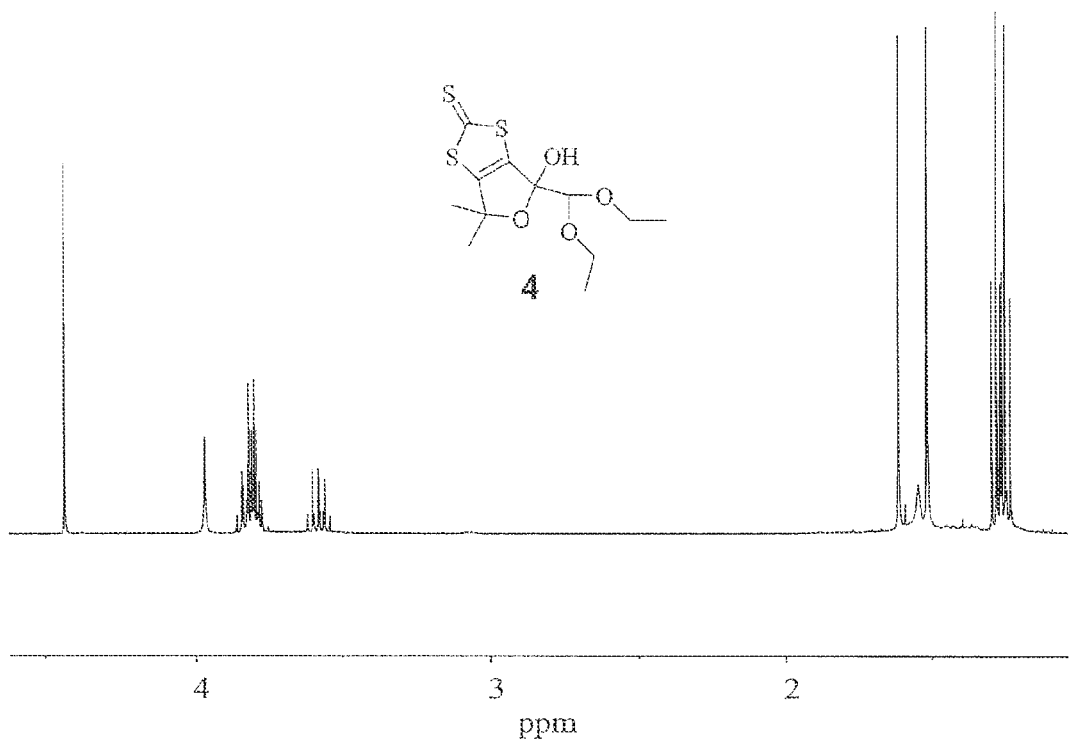
Figure 11. $^1$H NMR spectrum of compound 4 in CDCl$_3$.

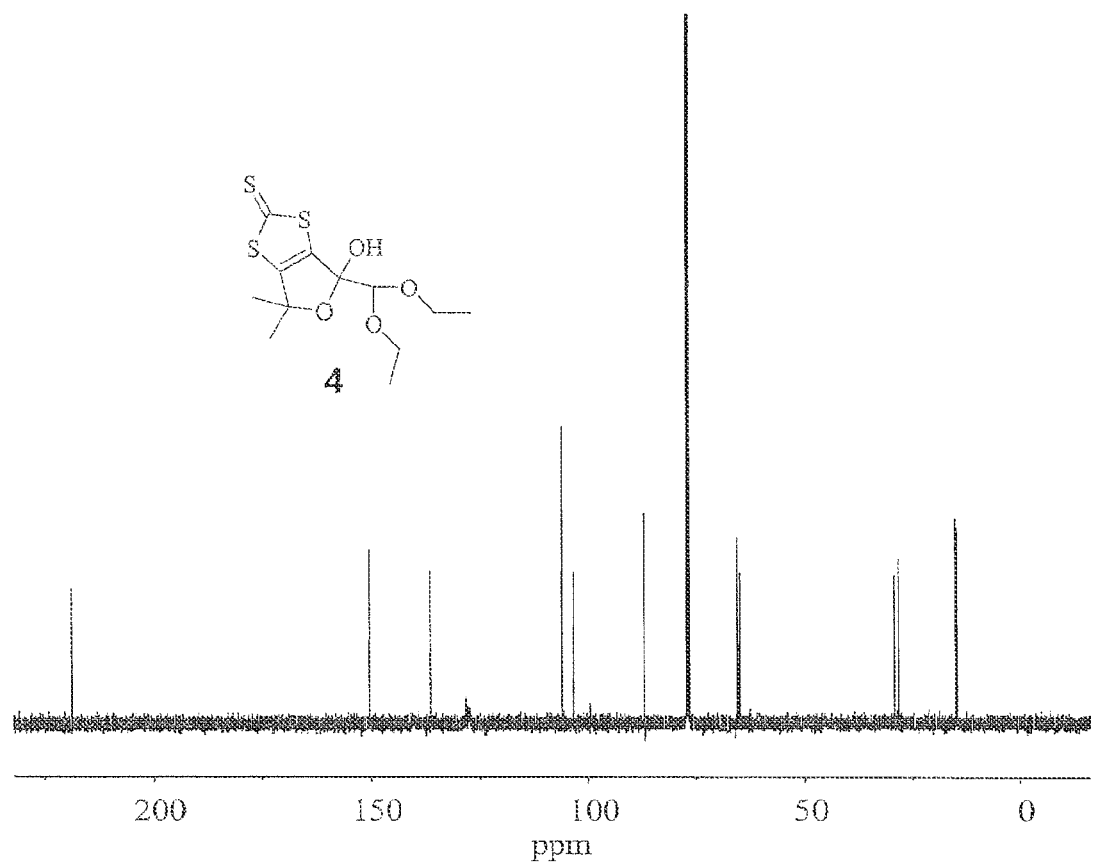
Figure 12. $^{13}$C NMR spectrum of compound 4 in CDCl$_3$.

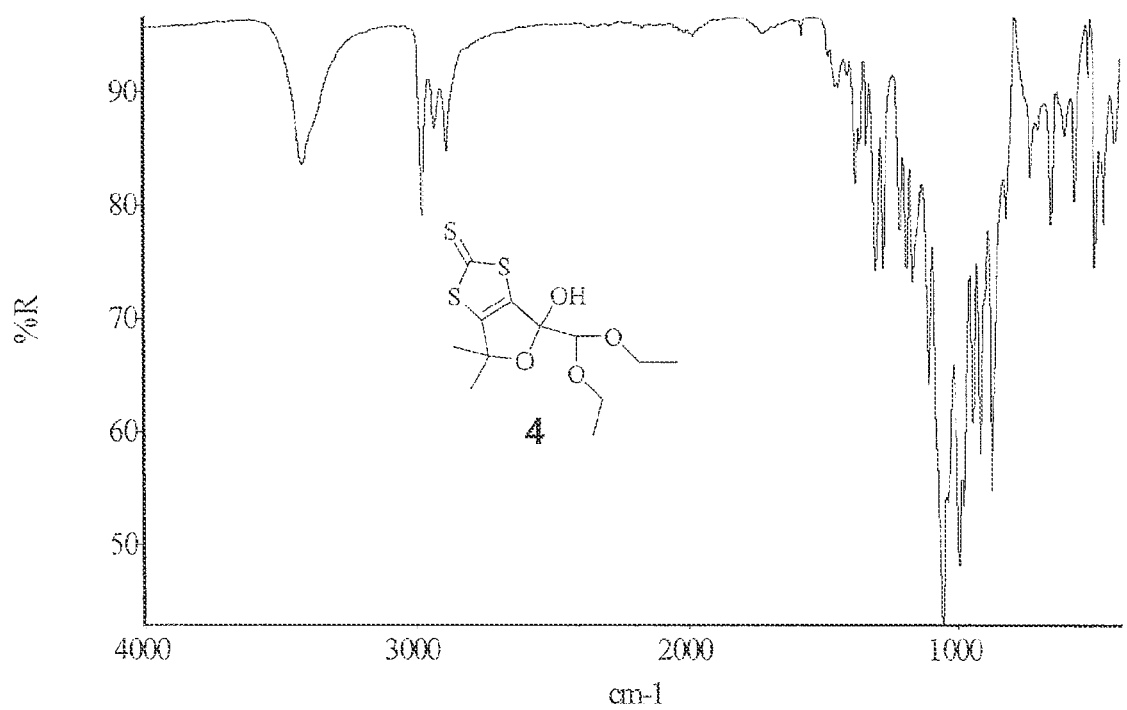
Figure 13. Infrared spectrum (neat) of compound 4.

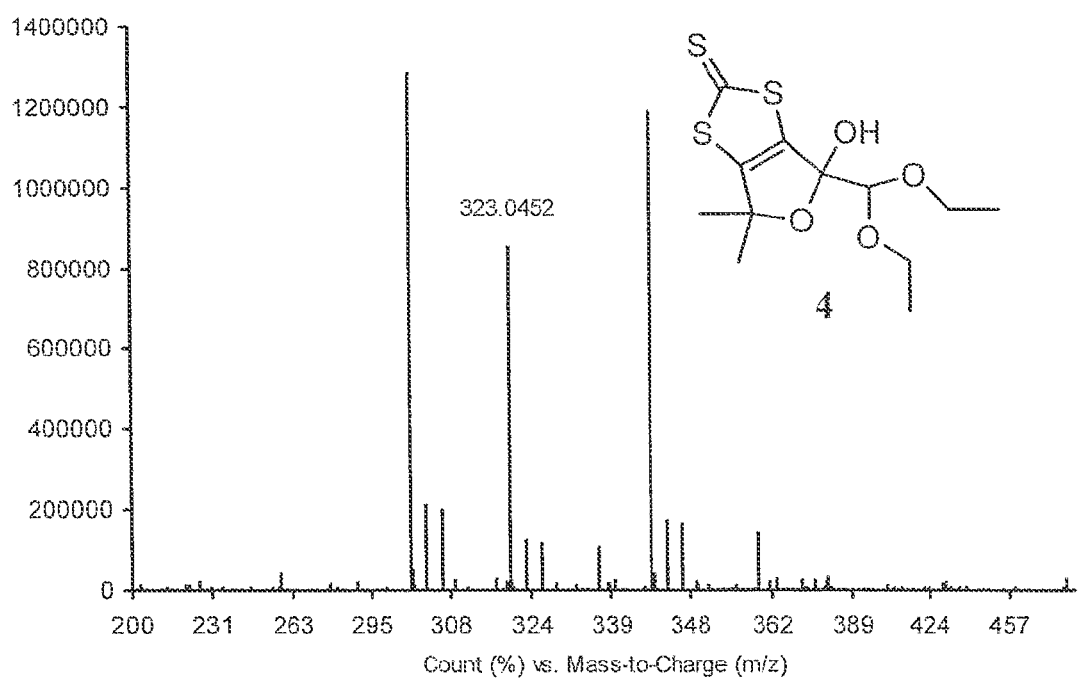
Figure 14. High resolution mass spectrum (ESI$^+$) of compound 4.

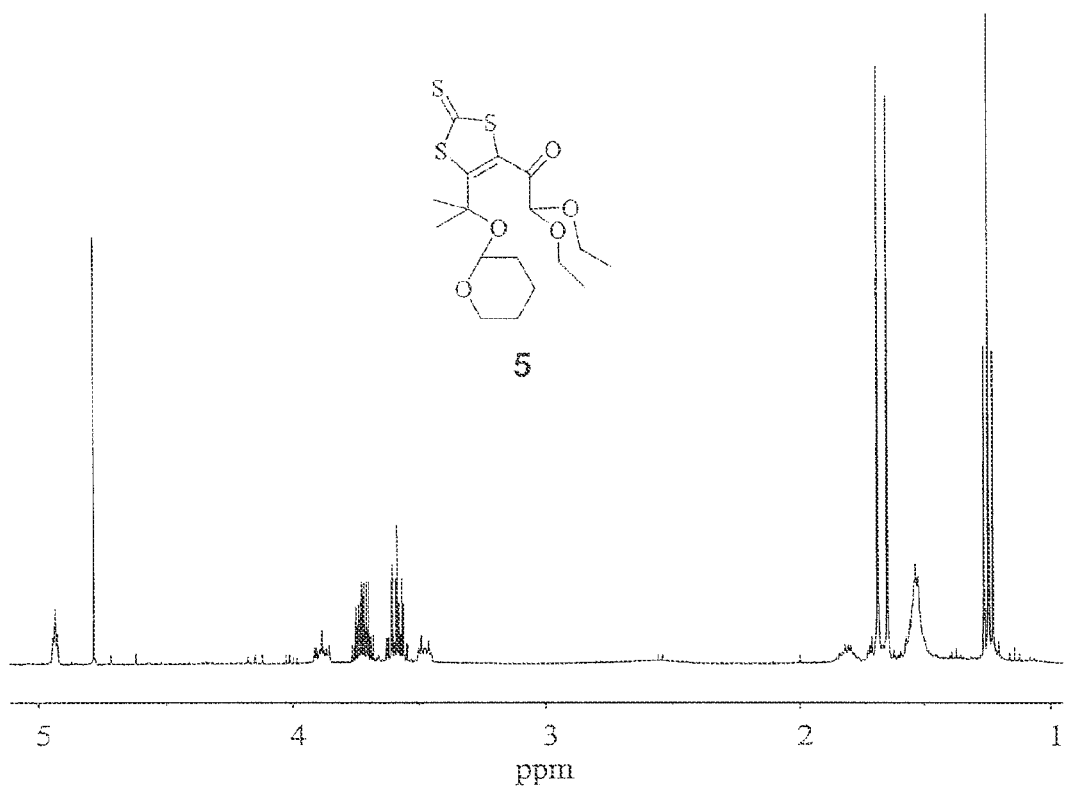
Figure 15. $^1$H NMR spectrum of compound 5 in CDCl$_3$.

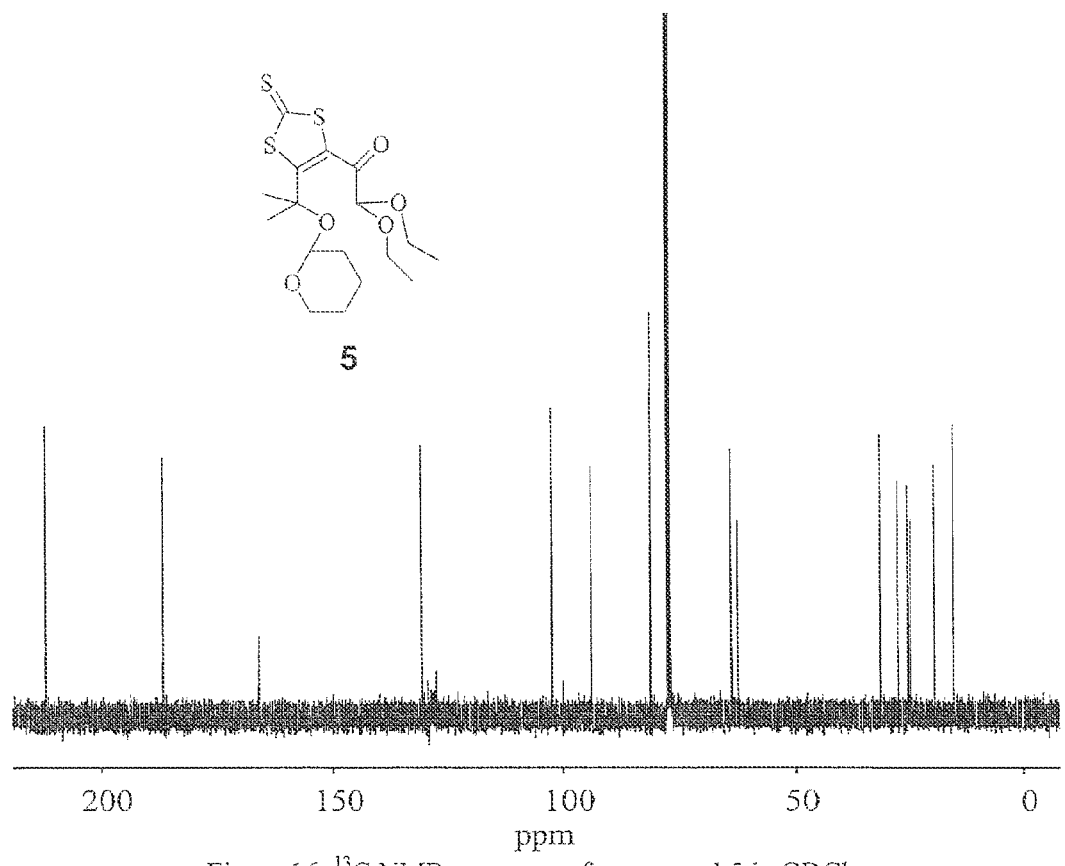
Figure 16. $^{13}$C NMR spectrum of compound 5 in CDCl$_3$.

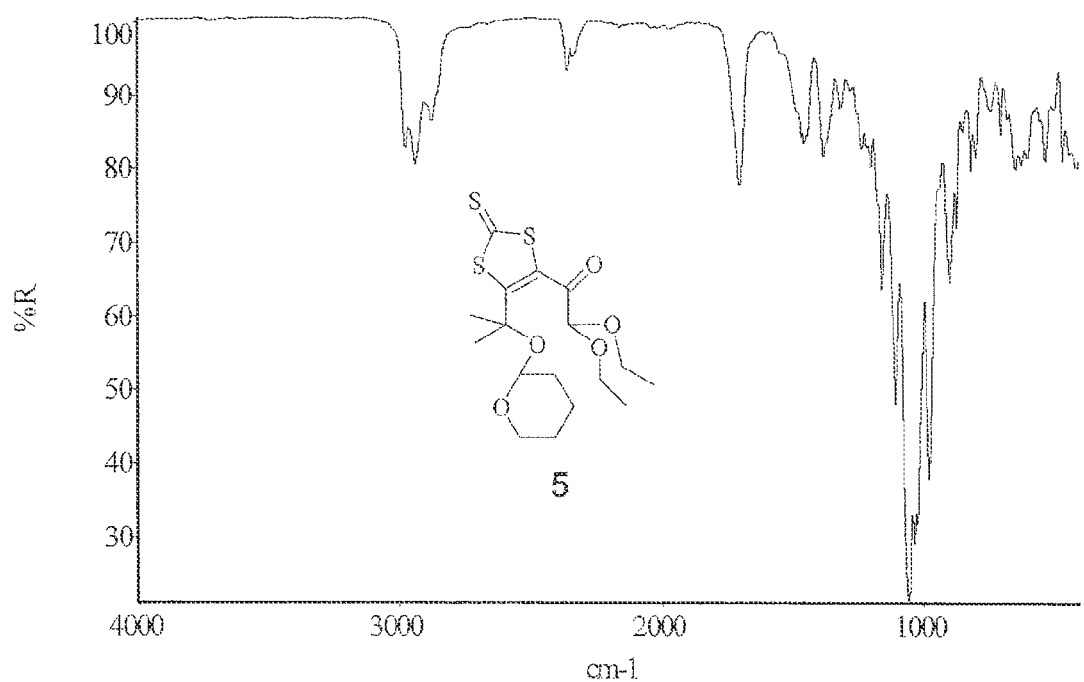
Figure 17. Infrared spectrum (neat) of compound 5.

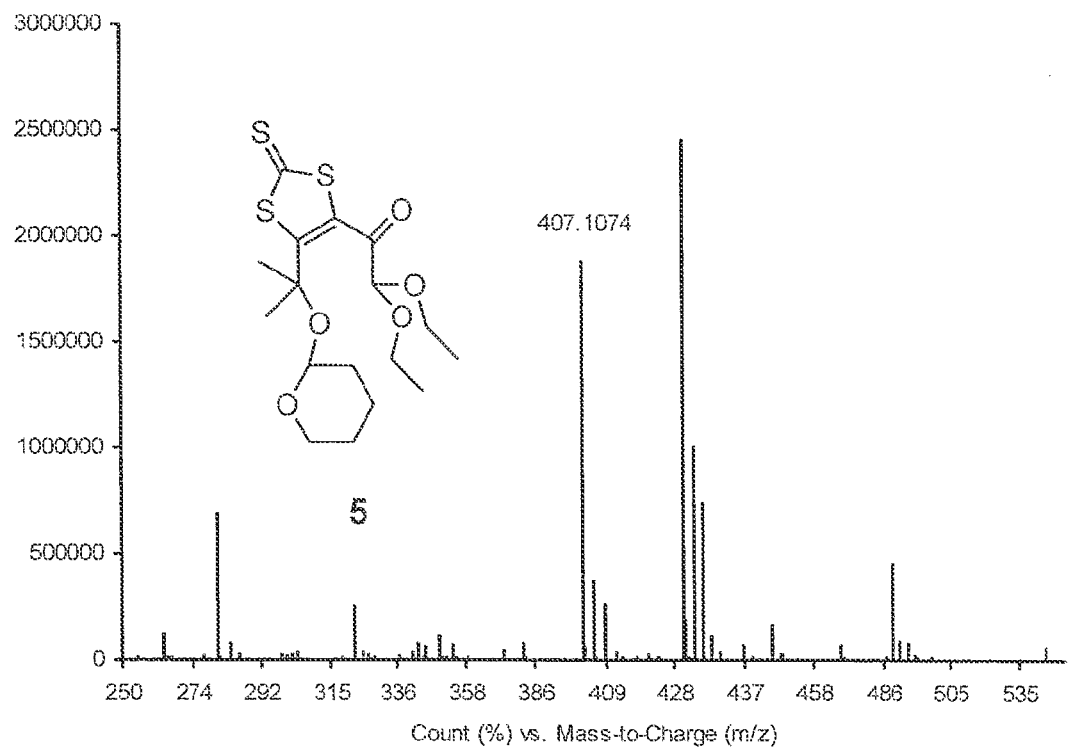
Figure 18. High resolution mass spectrum (ESI+) of compound 5.

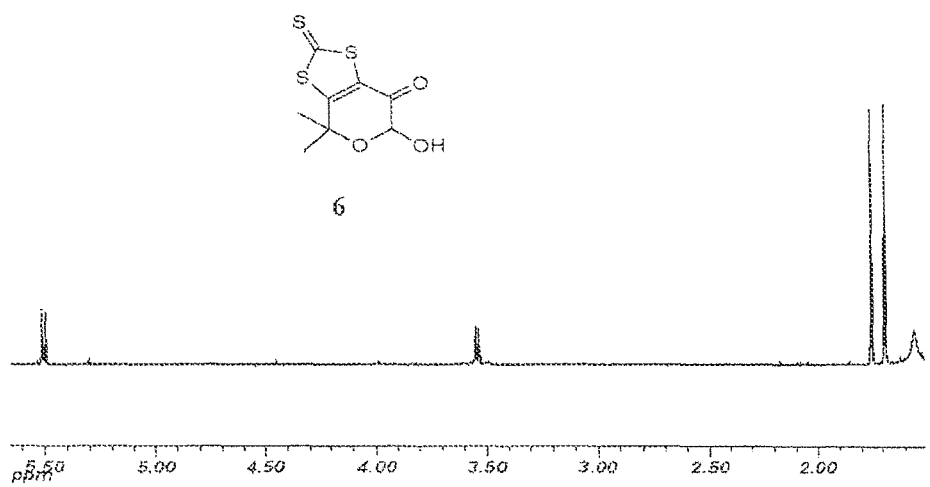
Figure 19. $^1$H NMR spectrum of compound 6 in CDCl$_3$.

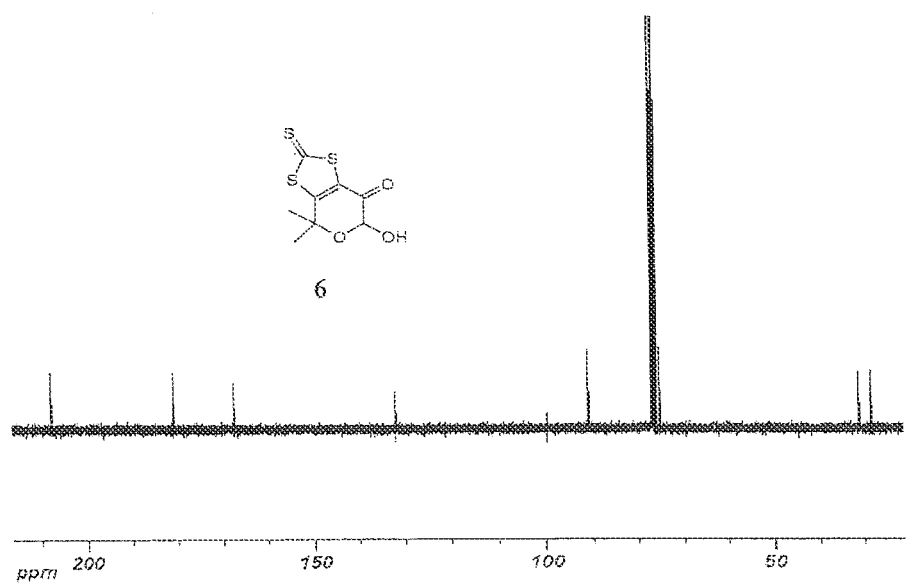
Figure 20. $^{13}$C NMR spectrum of compound 6 in CDCl$_3$.

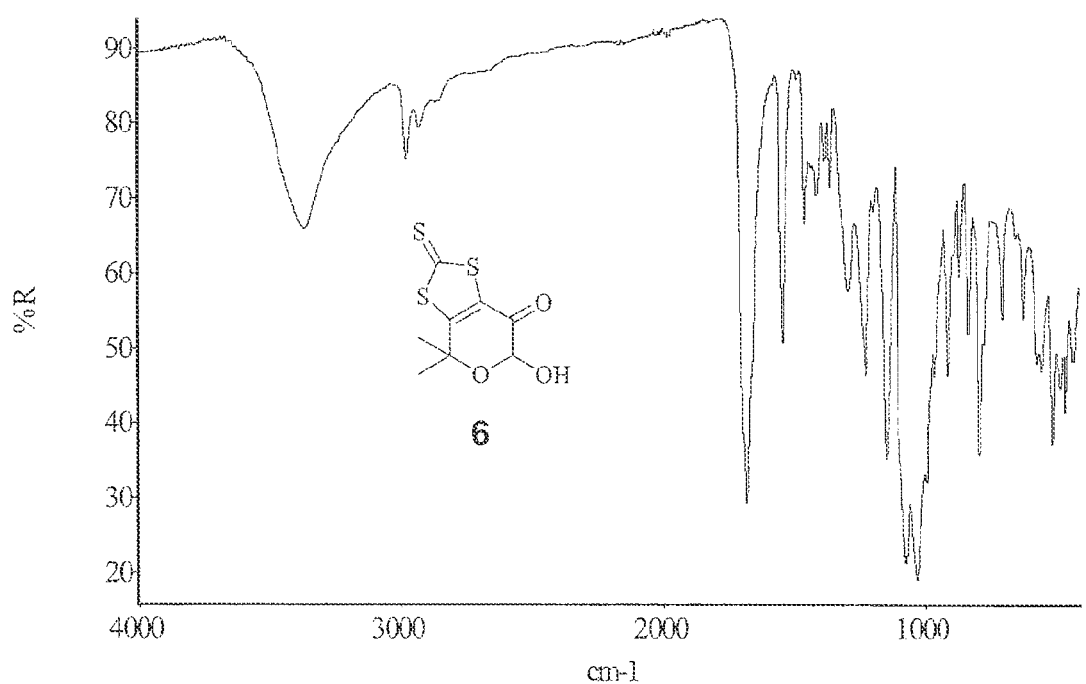
Figure 21. Infrared spectrum (neat) of compound 6.

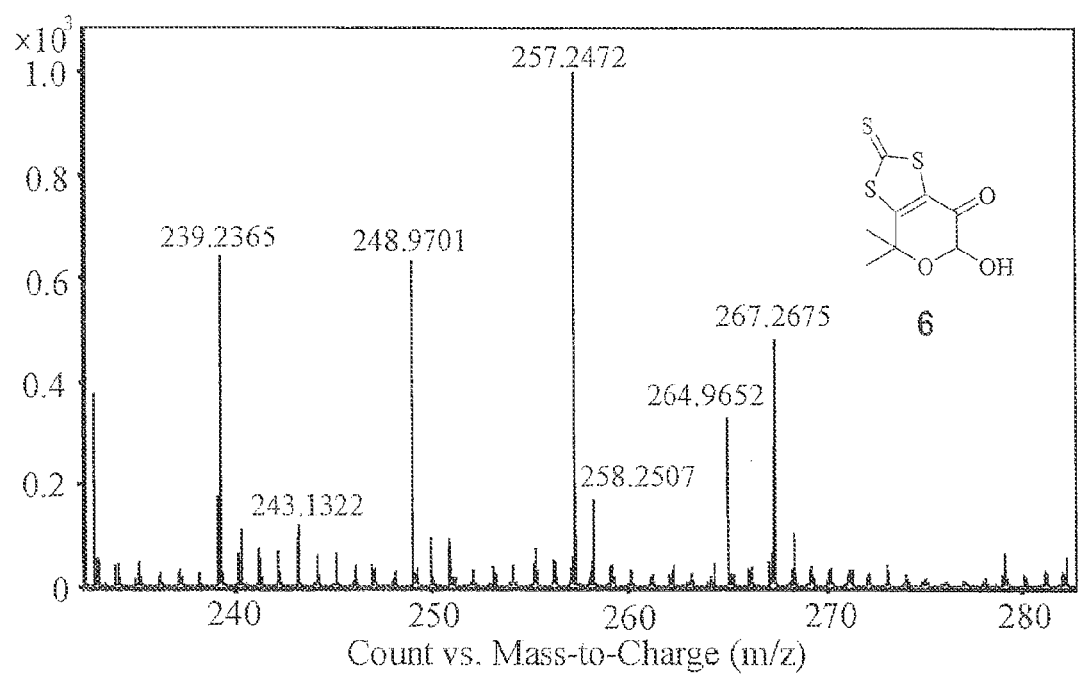
Figure 22. High resolution mass spectrum (APCI⁺) of compound 6.

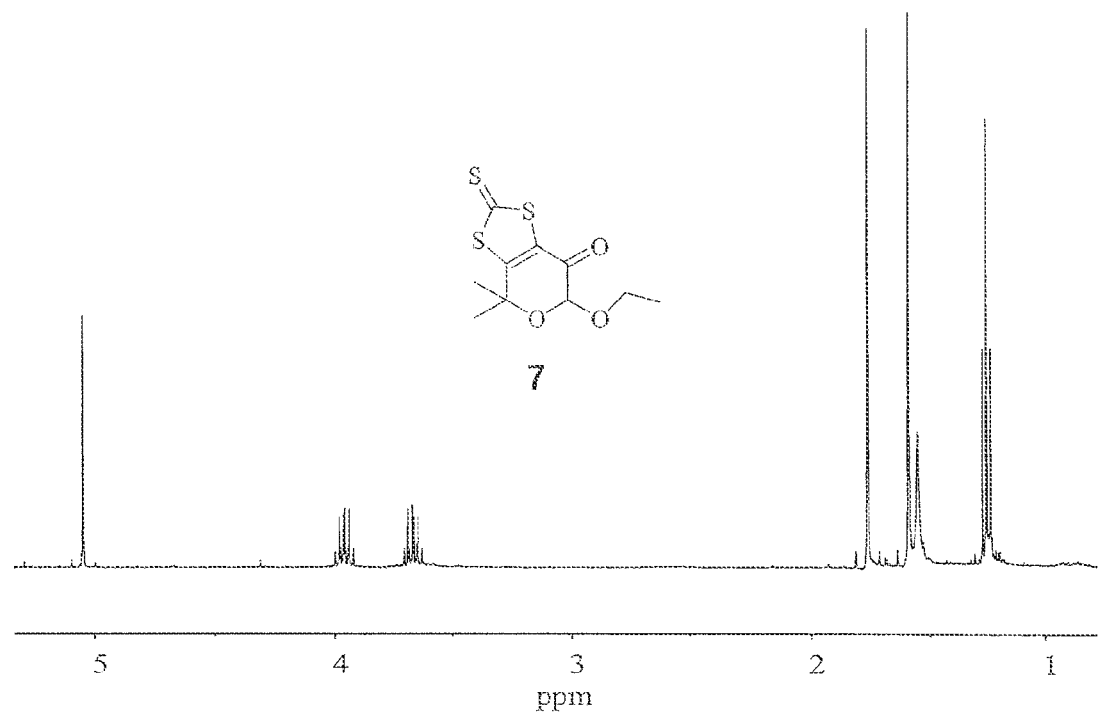
Figure 23. ¹H NMR spectrum of compound 7 in CDCl₃.

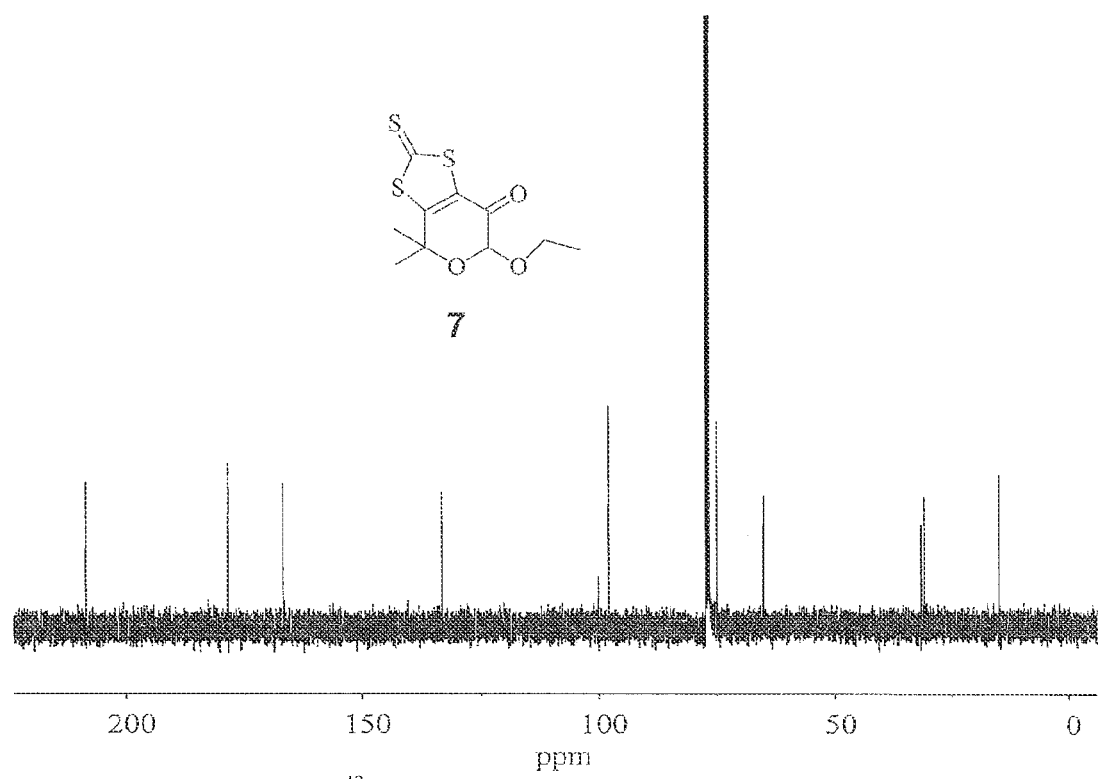
Figure 24. $^{13}$C NMR spectrum of compound 7 in CDCl$_3$.

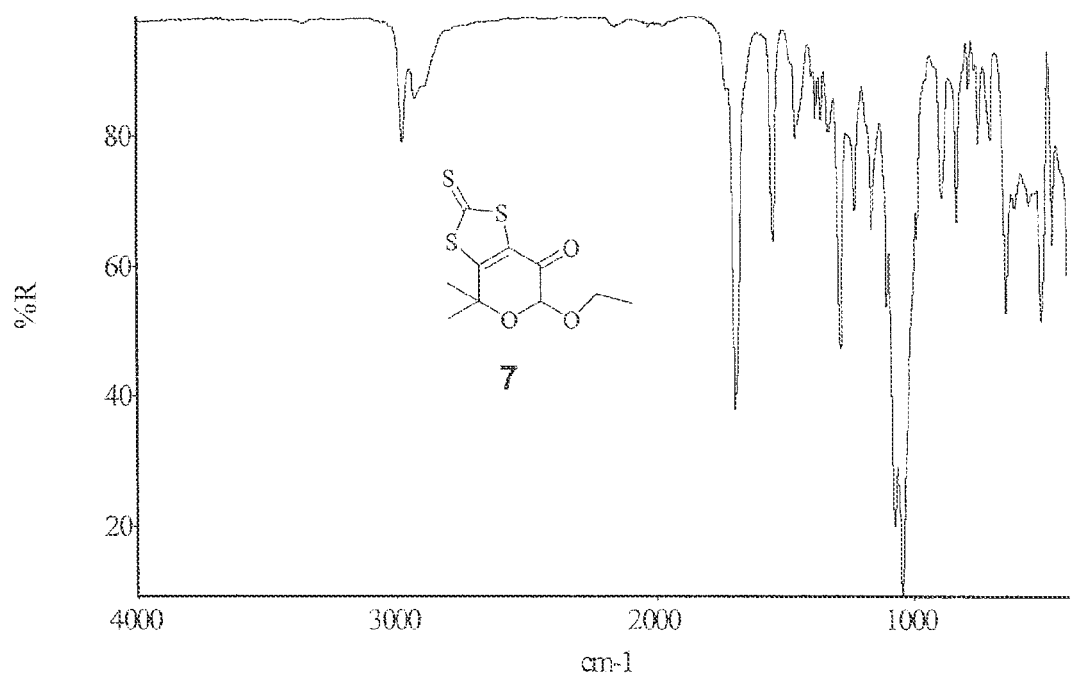
Figure 25. Infrared spectrum (neat) of compound 7.

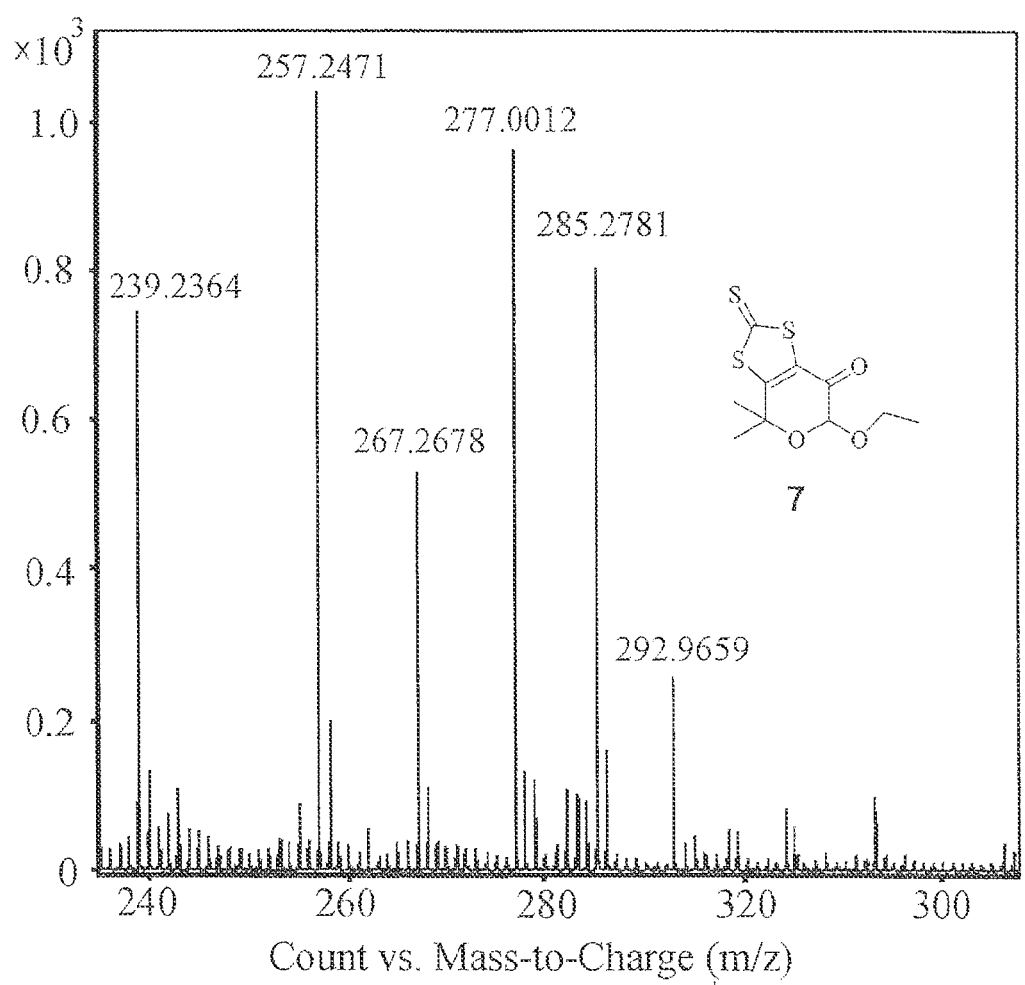
Figure 26. High resolution mass spectrum (APCI+) of compound 7.

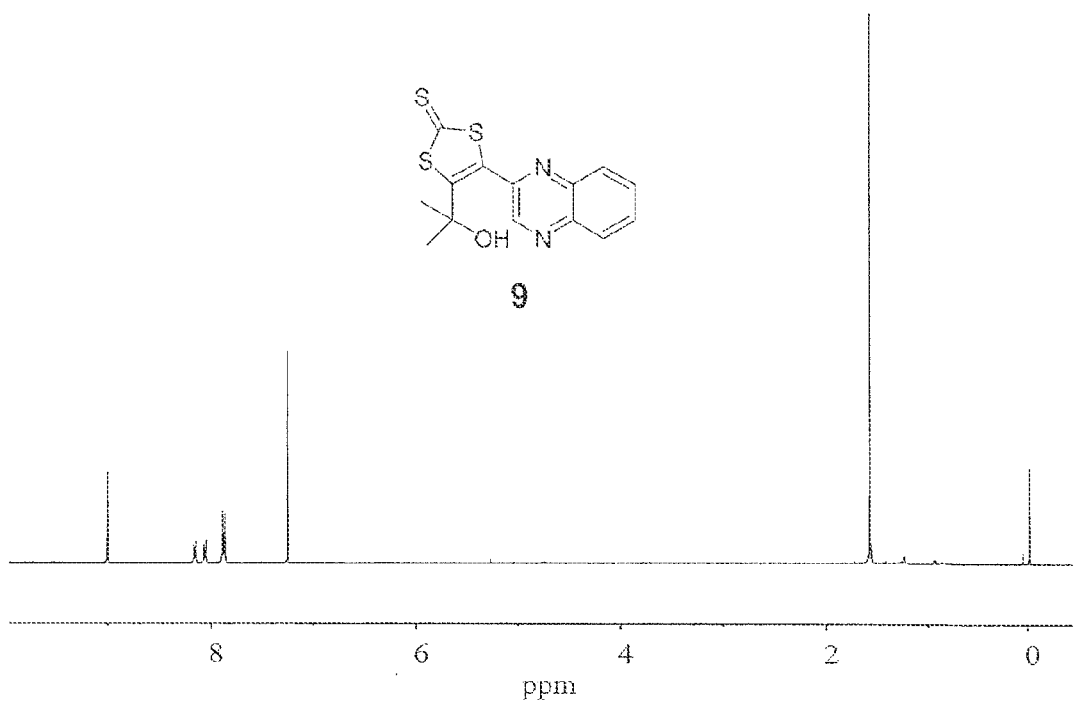
Figure 27. ¹H NMR spectrum of compound 9 in CDCl$_3$.

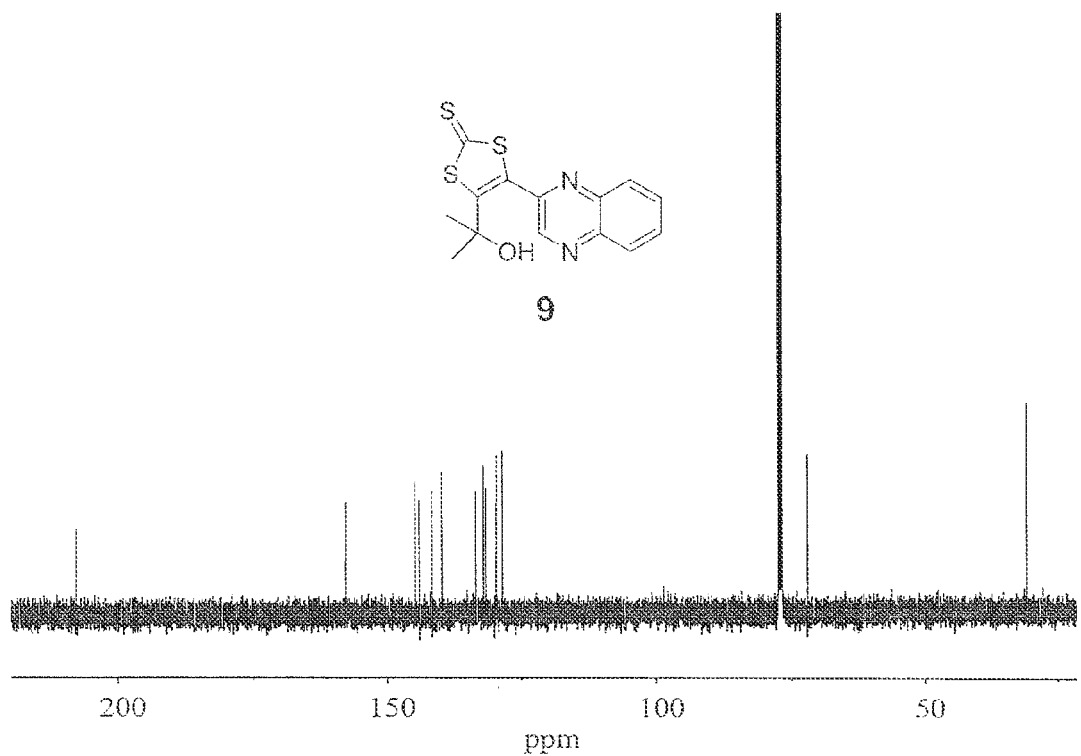
Figure 28. $^{13}$C NMR spectrum of compound 9 in CDCl$_3$.

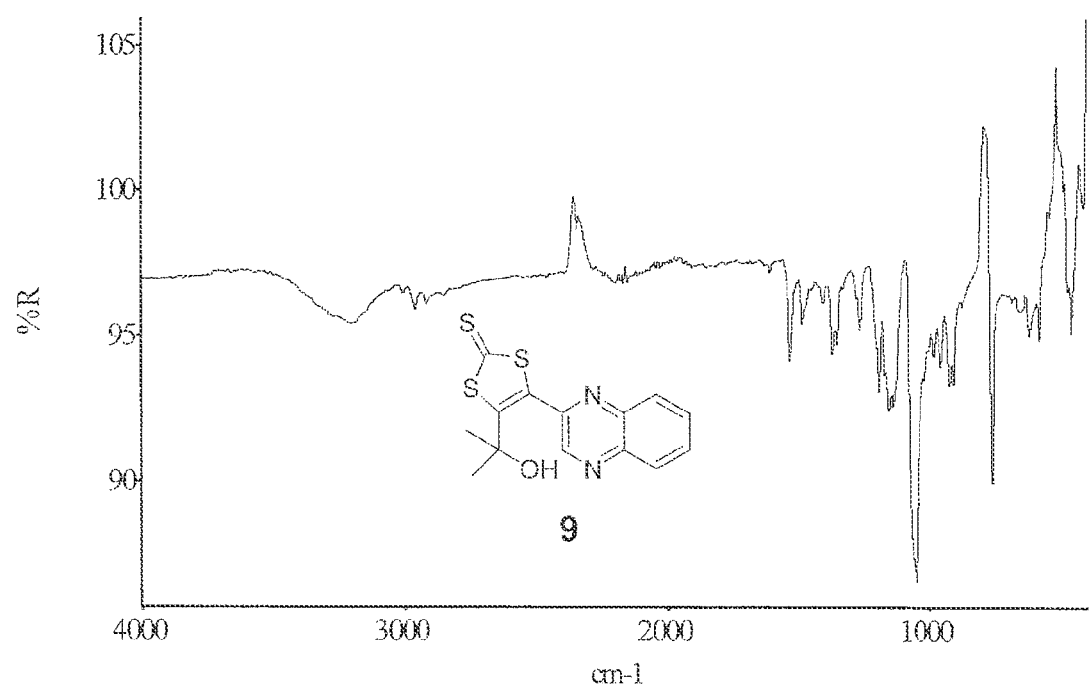
Figure 29. Infrared spectrum (neat) of compound 9.

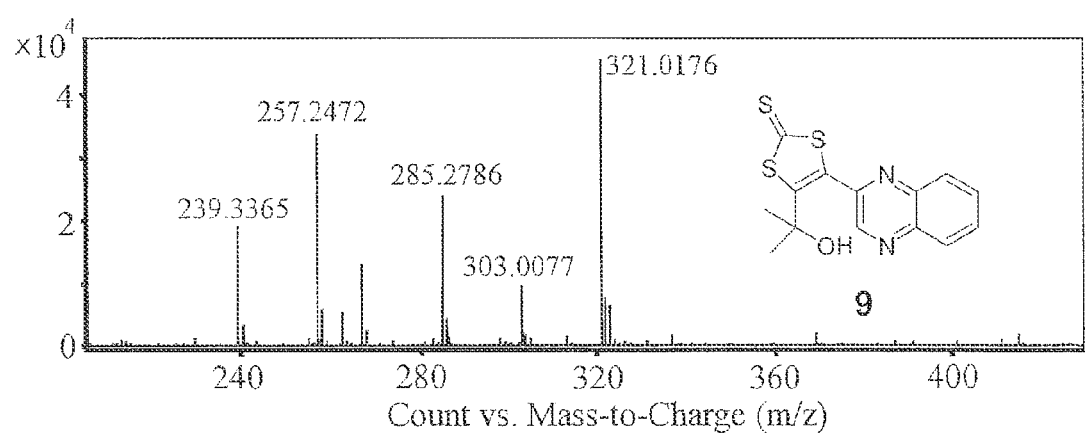
Figure 30. High resolution mass spectrum (APCI⁺) of compound 9.

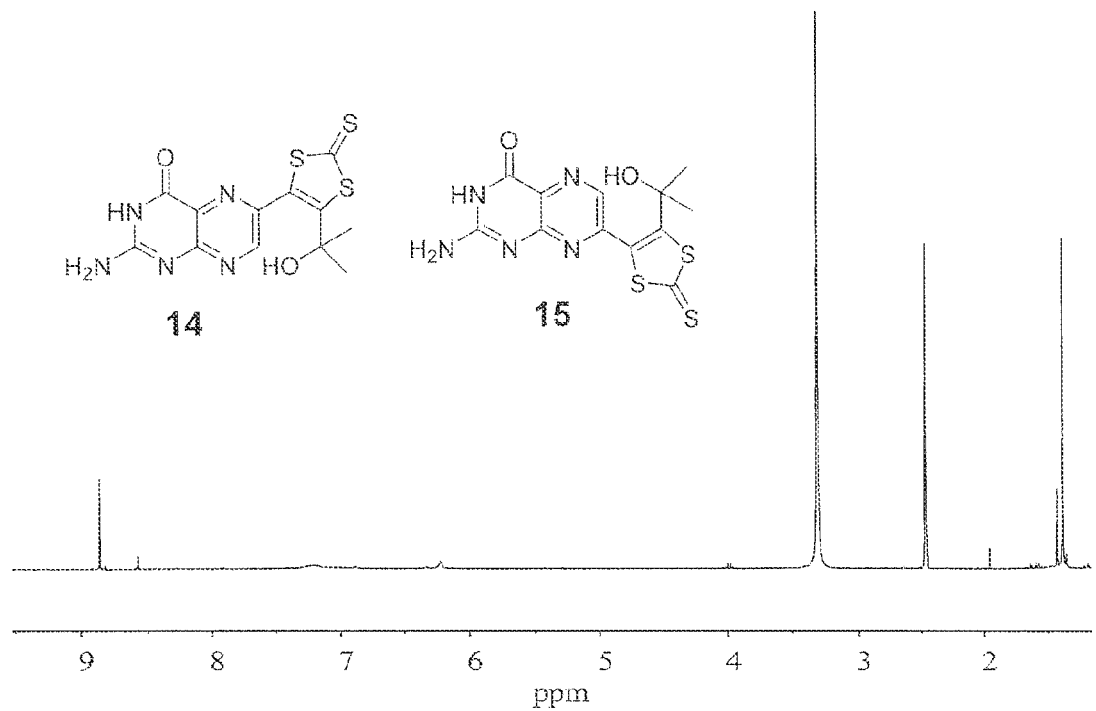
Figure 31. ¹H NMR spectrum of compound 14 and 15 in DMSO.

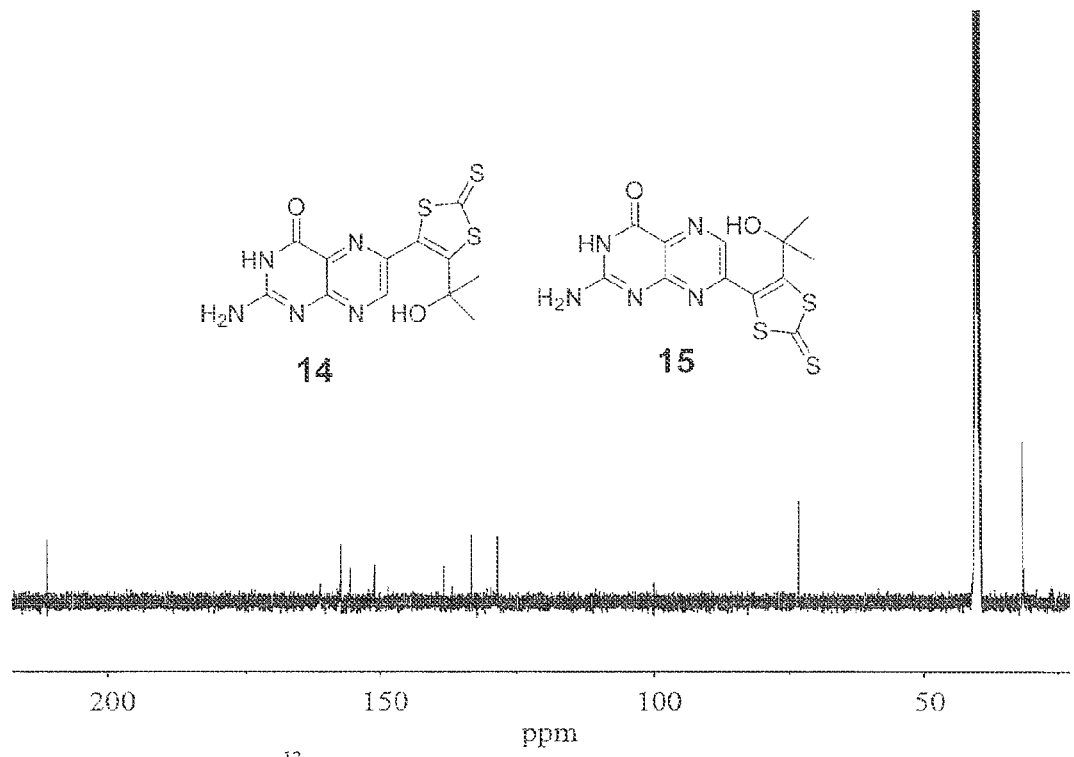
Figure 32. $^{13}$C NMR spectrum of compound 14 and 15 in DMSO.

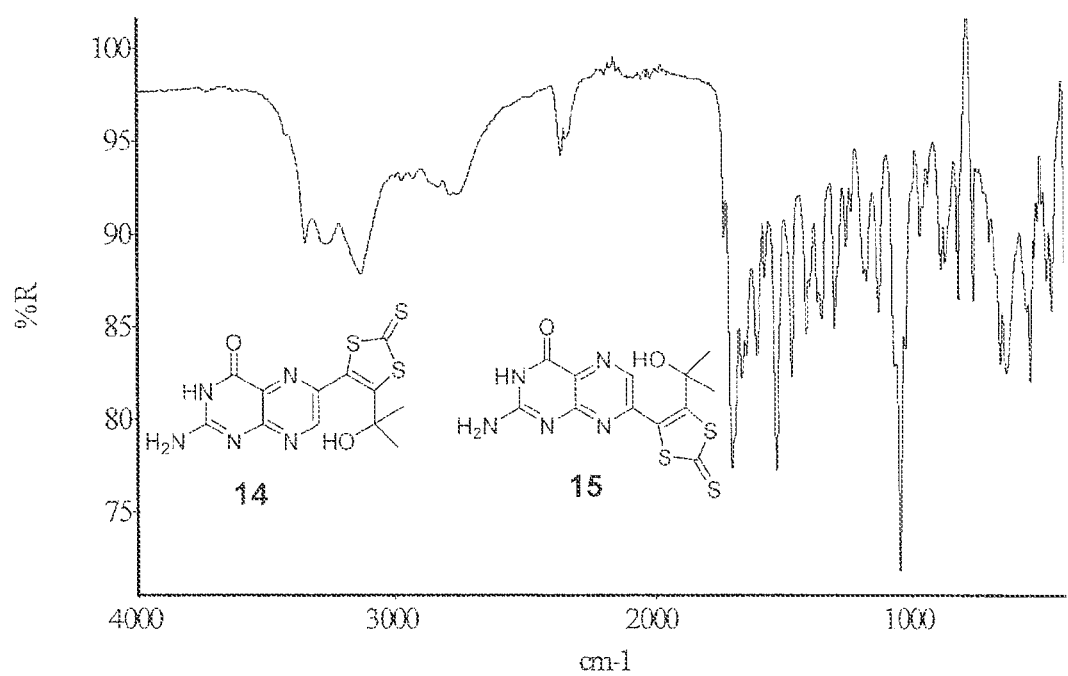
Figure 33. Infrared spectrum (neat) of compound 14 and 15.

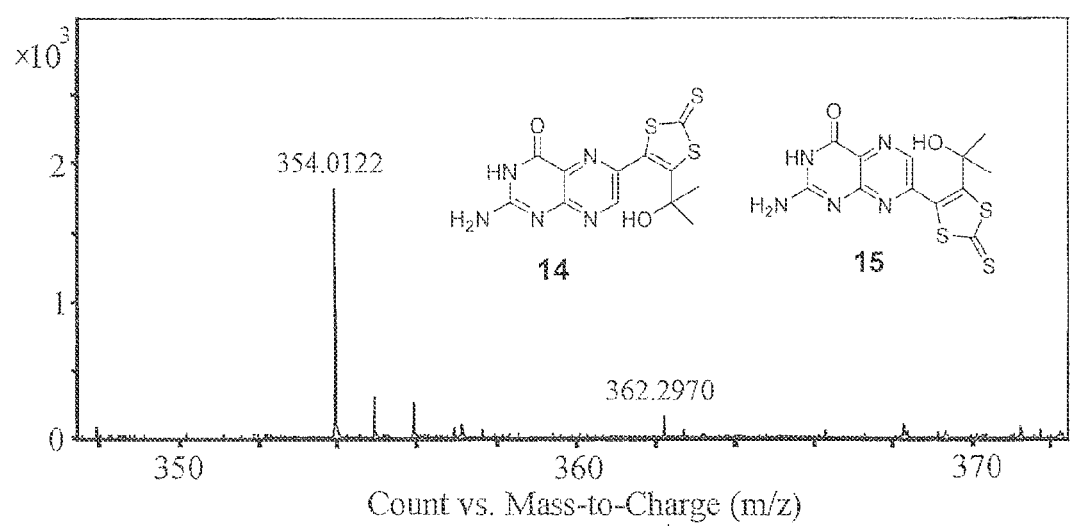
Figure 34. High resolution mass spectrum (ESI⁺) of compound 14 and 15.

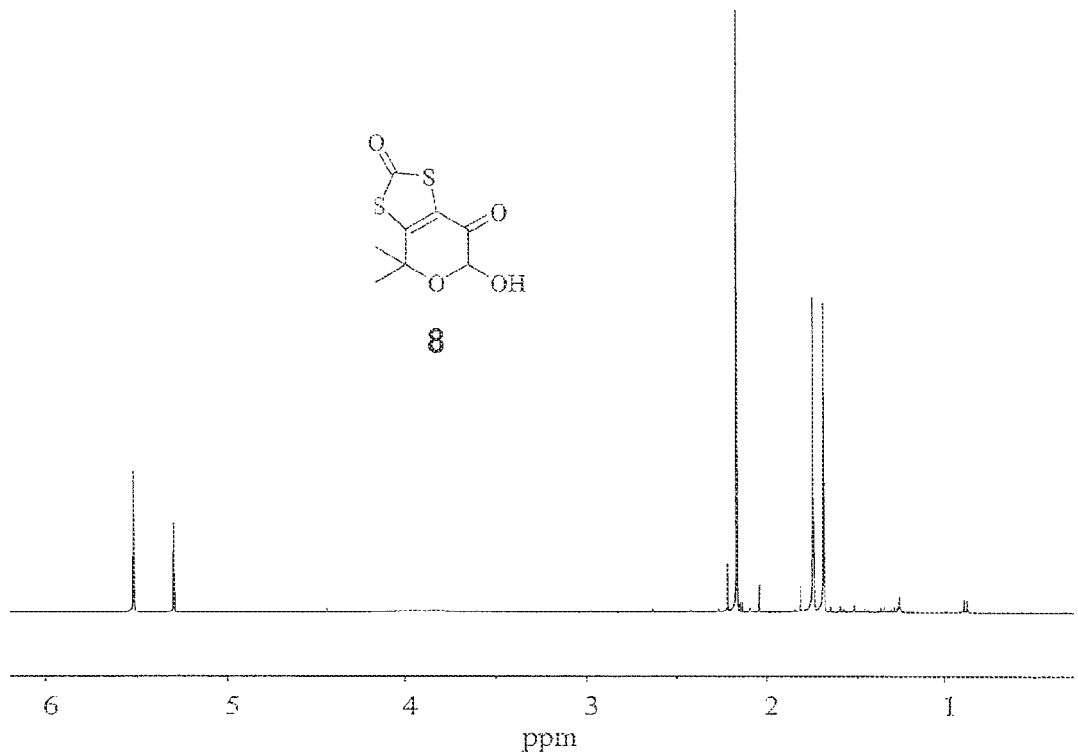
Figure 35. $^1$H NMR spectrum of compound 8 in CDCl$_3$.

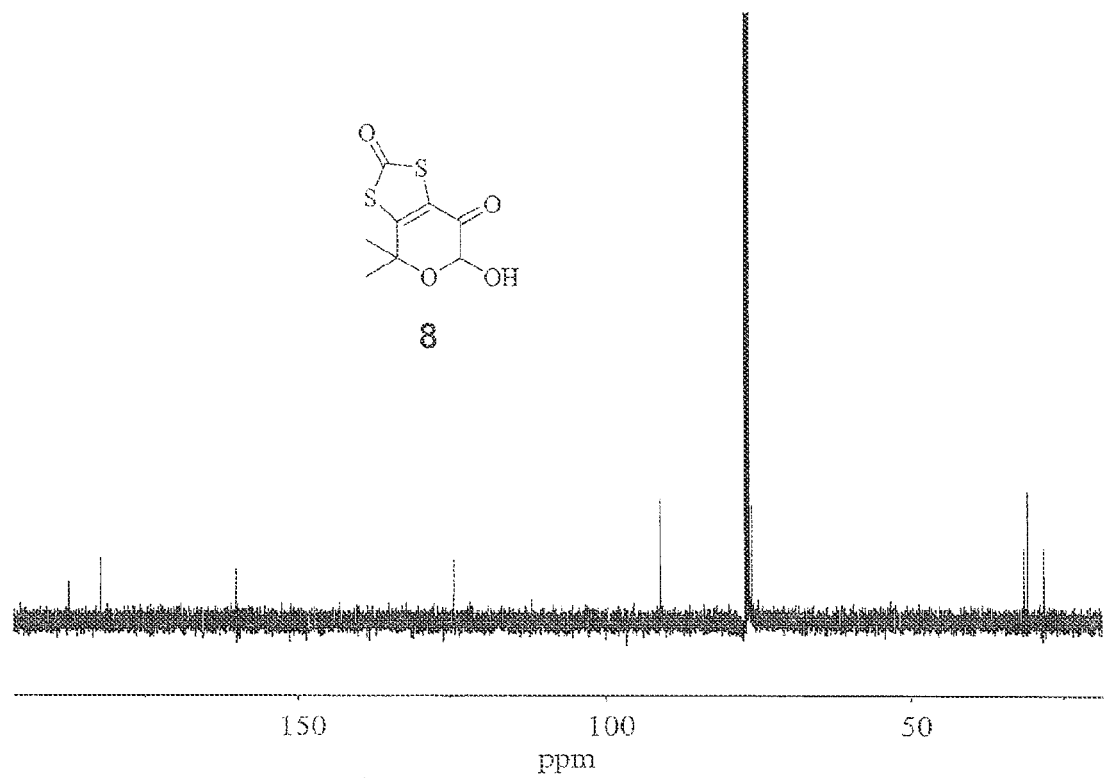
Figure 36. $^{13}$C NMR spectrum of compound 8 in CDCl$_3$.

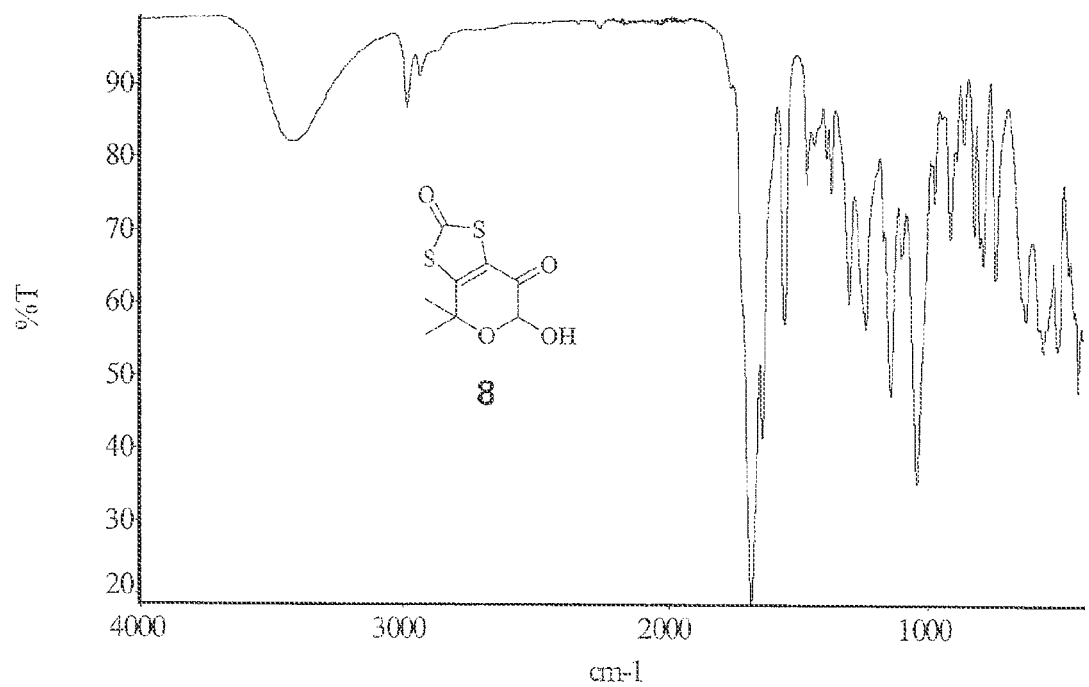
Figure 37. Infrared spectrum (neat) of compound 8.

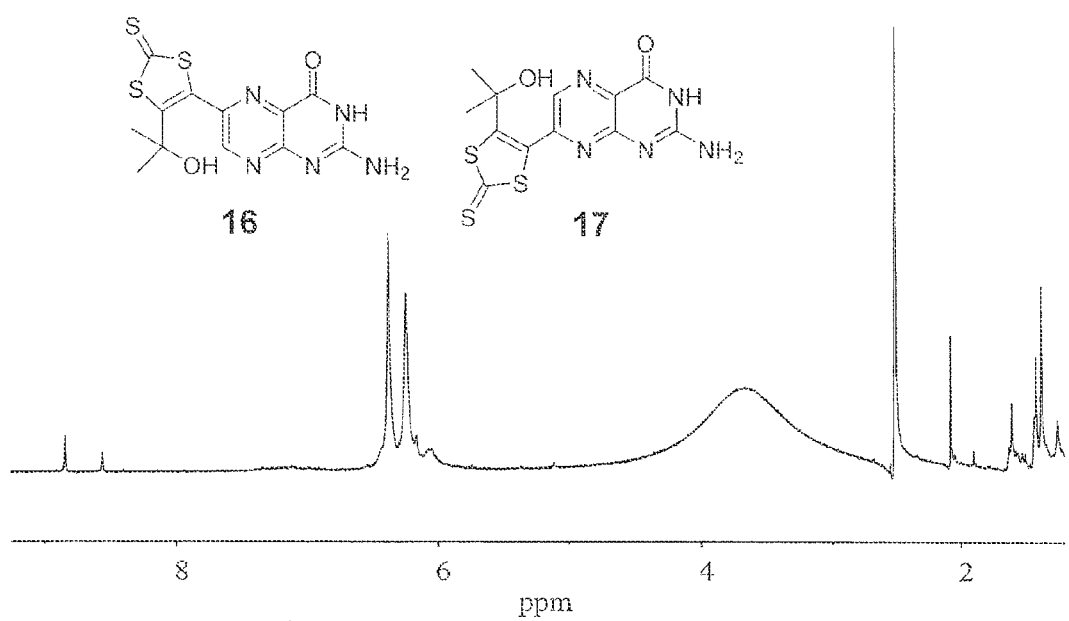
Figure 38. $^1$H NMR spectrum of compound 16 and 17 in DMSO.

COMPOSITION, SYNTHESIS, AND USE OF NEW SUBSTITUTED PYRAN AND PTERIN COMPOUNDS

CROSS-RELATED APPLICATIONS

This patent application is a divisional of, and claims priority to, patent application Ser. No. 13/735,511, filed on Jan. 7, 2013, entitled "Composition, Synthesis, and Use of New Substituted Pyran and Pterin Compounds", which is a divisional of, and claims priority to, patent application Ser. No. 13/072,092 filed on Mar. 25, 2011, entitled "Composition, Synthesis, and Use of New Substituted Pyran and Pterin Compounds" which issued as U.S. Pat. No. 8,378,123 on Feb. 19, 2013. Both, of which, are incorporated in their entirety by reference herein.

GOVERNMENT FUNDING

This invention was made with government support under grant #GM61555-04A1 awarded by the National Institutes of Health, National Institute of General Medical Sciences. The government has certain rights in the invention.

FIELD OF THE INVENTION

The present invention relates to new substituted pyran and pterin compounds, their synthesis and use. The new substituted pyran compounds can be used as a precursor in the synthesis of the new substituted pterin compounds. These new compounds are suitable for use in a wide variety of applications including, but not limited to, medicine and pharmaceuticals.

BACKGROUND OF THE INVENTION

Pterin is a heterocyclic compound composed of a pyrazine ring and a pyrimidine ring (a pteridine ring system). The pyrimidine ring includes a carbonyl oxygen and an amino group. Pterins are derivatives of 2-amino-4-oxopteridine with additional functional groups attached to the pyrazine ring. Pterins are known in the art and are used in a various applications. One of the most notable examples of pterin is folic acid. Another example is molybdopterin which is a substituted pteridine that binds molybdenum to give redox enzymes involved in biological hydroxylation and oxidation reactions. Pterins, substituted pterins, and derivatives thereof are of significant interest because of their potential uses in the fields of medicine and pharmaceuticals. It is contemplated that pterins can be used as a means for therapy in treating various medical conditions, such as cancer and molybdenum cofactor deficiency (MCD). Further, it is believed that pterins may possess antibacterial properties.

Pyran is a heterocyclic ring composed of five carbon atoms and one oxygen atom. There are many pyran derivatives that are known in the art as important biological molecules.

Molybdenum is an essential trace element for virtually all life forms. It is central to a cofactor for a number of enzymes that catalyze important chemical transformations. A biological form of molybdenum present in molybdenum-containing enzymes is known as the molybdenum cofactor. The molybdenum cofactor is a complicated molecule with multiple redox-active components delicately balanced having the following structure:

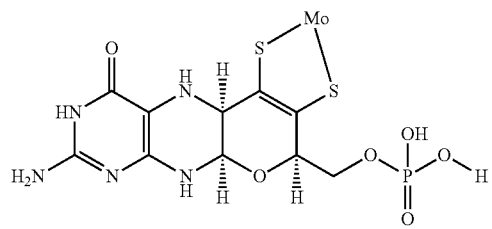

In some enzymes, the phosphate group substituent of the cofactor is modified with a dinucleotide. The chemical synthesis of the molybdenum cofactor and its precursors is very challenging.

An absence of or deficiency in molybdenum cofactor (known as MCD) in the human body can lead to serious illness and death. MCD is a lethal autosomal recessive disease for which treatment and cure is a focus of significant research efforts.

The biosynthetic pathway of molybdenum cofactor is a multi-step and evolutionarily conserved process involving four genes. Three of these four genes are linked to MCD. Patients are characterized by progressive neurological damage, leading to early childhood death in most cases. Symptoms are mainly caused by the sulfite oxidase (SO) enzyme deficiency. The SO enzymes remove toxic sulfite in the human body to protect the organs, particularly the brain, from an accumulation of sulfite. A deficiency of SO enzymes causes excess sulfite to accumulate in plasma and serum, it crosses the blood-brain barrier, and rapidly triggers neuronal death. Excess sulfite reacts with cystine, forming S-sulfocysteine, a potential agonist of glutamate receptors, which has been implicated for observed seizures, convulsions, contractions and twitching associated with MCD, causing damage of cortical neurons and loss of white matter.

There is a desire in the art to develop and synthesize new substituted pyrans and pterins for use in various applications including medicine and pharmaceuticals, such as, but not limited to, the treatment of MCD.

SUMMARY OF THE INVENTION

Various aspects provide for compounds. Other aspects relate to the synthesis of these compounds and their uses.

In one aspect, the present invention provides a compound comprising a structure:

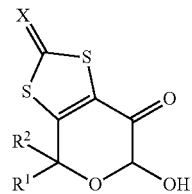

wherein X is selected from the group consisting of oxygen and sulfur, and, $R^1$ and $R^2$ are each independently selected from the group consisting of hydrogen, substituted and non-substituted, aliphatic and non-aliphatic hydrocarbon, branched and non-branched alkyl, cycloalkyl having one or more rings, aryl including benzyl, phenyl, thienyl, indoyl, heteroaryl, phosphate including organic and inorganic, combinations thereof, and derivatives thereof.

In another aspect, the present invention provides a method for preparing a compound having a structure:

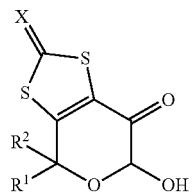

wherein X is selected from the group consisting of oxygen and sulfur and, $R^1$ and $R^2$ are each independently selected from the group consisting of hydrogen, substituted and non-substituted, aliphatic and non-aliphatic hydrocarbon, branched and non-branched alkyl, cycloalkyl having one or more rings, aryl including benzyl, phenyl, thienyl, indoyl, heteroaryl, phosphate including organic and inorganic, combinations thereof, and derivatives thereof. The method includes protecting an alcohol group of an acetylene, deprotecting a hydrogen of the acetylene forming a corresponding acetylide compound, condensing the acetylide compound with an ester to form a substituted acetylene, combining the substituted acetylene with a sulfurating agent to introduce a dithiolene group to form a dithiolene substituted furan compound, and treating the dithiolene substituted furan compound with an organic compound or a mixture of organic compounds to form a substituted pyran dithiolene compound.

In still another aspect, the present invention includes a compound comprising a structure selected from the group consisting of:

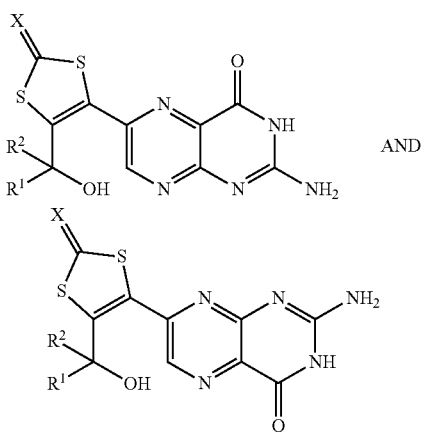

wherein X is selected from the group consisting of oxygen and sulfur and, $R^1$ and $R^2$ are each independently selected from the group consisting of hydrogen, substituted and non-substituted, aliphatic and non-aliphatic hydrocarbon, branched and non-branched alkyl, cycloalkyl having one or more rings, aryl including benzyl, phenyl, thienyl, indoyl, heteroaryl, phosphate including organic and inorganic, combinations thereof, and derivatives thereof.

In yet another aspect, the present invention provides a method of preparing a compound having a structure selected from the group consisting of:

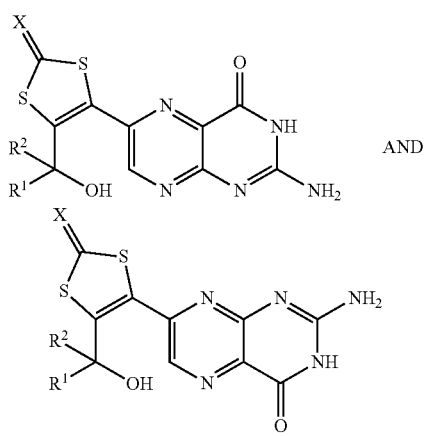

wherein X is selected from the group consisting of oxygen and sulfur and, $R^1$ and $R^2$ are each independently selected from the group consisting of hydrogen, substituted and non-substituted, aliphatic and non-aliphatic hydrocarbon, branched and non-branched alkyl, cycloalkyl having one or more rings, aryl including benzyl, phenyl, thienyl, indoyl, heteroaryl, phosphate including organic and inorganic, combinations thereof, and derivatives thereof. The method includes starting with a precursor compound having a structure:

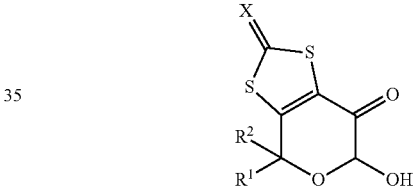

wherein X is selected from the group consisting of oxygen and sulfur and, $R^1$ and $R^2$ are each independently selected from the group consisting of hydrogen, substituted and non-substituted, aliphatic and non-aliphatic hydrocarbon, branched and non-branched alkyl, cycloalkyl having one or more rings, aryl including benzyl, phenyl, thienyl, indoyl, heteroaryl, phosphate including organic and inorganic, combinations thereof, and derivatives thereof, treating the precursor compound with o-phenylenediamine to form an open-ring compound, subjecting the open-ring compound to electrophilic activation leading to a corresponding ring closed quinoxaline derivative, and combining the quinoxaline derivative with pyrimidine in a condensation reaction to form the compound.

In another aspect, the present invention provides a therapeutic composition including the new substituted pterin compound of the present invention.

In yet another aspect, the present invention provides a method of treating molybdenum cofactor deficiency including administering a therapeutically effective amount of the new substituted pterin compound of the present invention.

BRIEF DESCRIPTION OF THE DRAWINGS

The various embodiments of the present disclosure may be better understood when read with reference to the following figures.

FIG. 1 illustrates the synthesis of a substituted pyran-dithiolene precursor compound.

FIG. 2 illustrates the synthesis of substituted quinoxaline and pterin compounds.

FIG. 3 illustrates $^1$H NMR spectrum of compound 2 in $CDCl_3$.

FIG. 4 illustrates $^{13}$C NMR spectrum of compound 2 in $CDCl_3$.

FIG. 5 illustrates infrared spectrum (neat) of compound 2.

FIG. 6 illustrates infrared spectrum (neat) of 4-phenyl-1,3-dithiolane-2-thione.

FIG. 7 illustrates $^1$H NMR spectrum of compound 3 in $CDCl_3$.

FIG. 8 illustrates $^{13}$C NMR spectrum of compound 3 in $CDCl_3$.

FIG. 9 illustrates infrared spectrum (neat) of compound 5.

FIG. 10 illustrates high resolution mass spectrum (ESI$^+$) of compound 3.

FIG. 11 illustrates $^1$H NMR spectrum of compound 4 in $CDCl_3$.

FIG. 12 illustrates $^{13}$C NMR spectrum of compound 4 in $CDCl_3$.

FIG. 13 illustrates infrared spectrum (neat) of compound 4.

FIG. 14 illustrates high resolution mass spectrum (ESI$^+$) of compound 4.

FIG. 15 illustrates $^1$H NMR spectrum of compound 5 in $CDCl_3$.

FIG. 16 illustrates $^{13}$C NMR spectrum of compound 5 in $CDCl_3$.

FIG. 17 illustrates infrared spectrum (neat) of compound 5.

FIG. 18 illustrates high resolution mass spectrum (ESI$^+$) of compound 5.

FIG. 19 illustrates $^1$H NMR spectrum of compound 6 in $CDCl_3$.

FIG. 20 illustrates $^{13}$C NMR spectrum of compound 6 in $CDCl_3$.

FIG. 21 illustrates infrared spectrum (neat) of compound 6.

FIG. 22 illustrates high resolution mass spectrum (APCI$^+$) of compound 6.

FIG. 23 illustrates $^1$H NMR spectrum of compound 7 in $CDCl_3$.

FIG. 24 illustrates $^{13}$C NMR spectrum of compound 7 in $CDCl_3$.

FIG. 25 illustrates infrared spectrum (neat) of compound 7.

FIG. 26 illustrates high resolution mass spectrum (APCI$^+$) of compound 7.

FIG. 27 illustrates $^1$H NMR spectrum of compound 9 in $CDCl_3$.

FIG. 28 illustrates $^{13}$C NMR spectrum of compound 9 in $CDCl_3$.

FIG. 29 illustrates infrared spectrum (neat) of compound 9.

FIG. 30 illustrates high resolution mass spectrum (APCI$^+$) of compound 9.

FIG. 31 illustrates $^1$H NMR spectrum of compounds 14 and 15 in DMSO.

FIG. 32 illustrates $^{13}$C NMR spectrum of compounds 14 and 15 in DMSO.

FIG. 33 illustrates infrared spectrum (neat) of compounds 14 and 15.

FIG. 34 illustrates high resolution mass spectrum (ESI$^+$) of compounds 14 and 15.

FIG. 35 illustrates $^1$H NMR spectrum of compound 8 in $CDCl_3$.

FIG. 36 illustrates $^{13}$C NMR spectrum of compound 8 in $CDCl_3$.

FIG. 37 illustrates infrared spectrum (neat) of compound 8.

FIG. 38 illustrates $^1$H NMR spectrum of compounds 16 and 17 in DMSO.

DETAILED DESCRIPTION OF THE INVENTION

The present invention relates to a new substituted pyran compound and its analogs that may be synthesized from readily available materials. This new compound can be used in various applications and in one embodiment, is used as a precursor or starting material to synthesize a new substituted pterin compound and its analogs. The substituted pyran compound includes a dithiolene group. The substituted pterin compound includes pyrimidine, pyrazine and dithiolene. The structures of these compounds are designed with the flexibility to have multiple substitution patterns. These compounds can have various uses and, in particular, are suitable for the medical and pharmaceutical fields.

Other than the operating examples, or where otherwise indicated, all numbers expressing quantities of ingredients, processing conditions and the like used in the specification and claims are to be understood as being modified in all instances by the term "about". Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the disclosure are approximations, the numerical values set forth in the specific examples are reported as precisely as possible. Any numerical values, however, may contain certain errors, such as, for example, equipment and/or operator error, necessarily resulting from the standard deviation found in their respective testing measurements.

Also, it should be understood that any numerical range recited herein is intended to include all sub-ranges subsumed therein. For example, a range of "1 to 10" is intended to include all sub-ranges between (and including) the recited minimum value of 1 and the recited maximum value of 10, that is, having a minimum value equal to or greater than 1 and a maximum value of less than or equal to 10.

The present disclosure describes several different features and aspects of the invention with reference to various exemplary non-limiting embodiments. It is understood, however, that the invention embraces numerous alternative embodiments, which may be accomplished by combining any of the different features, aspects, and embodiments described herein in any combination that one of ordinary skill in the art would find useful.

In one aspect, the present disclosure relates to the development of a new substituted pyran compound having a structure including at least two fused rings. One ring includes a five-membered ring (e.g., protected dithiolene) and another ring includes a six-membered ring (e.g., pyran). The general structure of the new substituted pyran compound is represented by structure I.

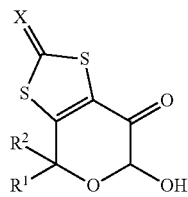

(I)

In structure I, X is selected from oxygen (O) and sulfur (S). Further, in structure I, $R^1$ and $R^2$ are each independently selected from hydrogen, substituted and non-substituted, aliphatic and non-aliphatic hydrocarbon, branched and non-branched alkyl, such as $C_1$-$C_6$ alkyl, hydroxy $C_1$-$C_6$ alkyl, alkenyl, alkynyl, cycloalkyl having one or more rings, aryl including benzyl, phenyl, thienyl, indoyl, heteroaryl, phosphate including organic and inorganic, combinations thereof, and derivatives thereof. $R^1$ and $R^2$ may be the same or different. As used herein, the term "aryl" includes an aromatic ring (i.e., a single aromatic ring) or a ring system (i.e., a polycyclic aromatic ring system) in which all ring atoms are carbon. In one embodiment, $R^1$ and $R^2$ are each independently selected from methyl ($CH_3$), hydroxyl ethyl, organic phosphate, and inorganic phosphate. In another embodiment, $R^1$ and $R^2$ are both methyl or hydroxy ethyl or phosphate.

According to various embodiments, the substituted pyran having the general structure of structure I, may be readily synthesized using organic chemistry techniques. For example, the synthesis of various embodiments of the substituted pyran is described herein. It should be noted that the featured embodiments are intended to be exemplary and are in no way limiting to the scope of the precursor as described herein. The synthetic approach for the substituted pyran includes beginning with an acetylene compound. The acetylene compound can be selected from those that are known in the art and commercially available. The acetylene compound is soluble in an organic solvent. The organic solvent can be selected from those that are known in the art and commercially available. In one embodiment, the organic solvent is dichloromethane. In another embodiment, the acetylene compound has the general structure represented by structure II.

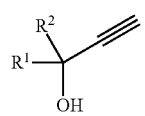

(II)

In structure II, $R^1$ and $R^2$ are each independently selected from hydrogen, substituted and non-substituted, aliphatic and non-aliphatic hydrocarbon, branched and non-branched alkyl, such as $C_1$-$C_6$ alkyl, hydroxy $C_1$-$C_6$ alkyl, alkenyl, alkynyl, cycloalkyl having one or more rings, aryl including benzyl, phenyl, thienyl, indoyl, heteroaryl, phosphate including organic and inorganic, combinations thereof, and derivatives thereof. $R^1$ and $R^2$ may be the same or different. As used herein, the term "aryl" includes an aromatic ring (i.e., a single aromatic ring) or a ring system (i.e., a polycyclic aromatic ring system) in which all ring atoms are carbon. In one embodiment, $R^1$ and $R^2$ are each independently selected from methyl ($CH_3$), hydroxyl ethyl, organic phosphate, and inorganic phosphate. In another embodiment, $R^1$ and $R^2$ are both methyl or hydroxy ethyl or phosphate.

Further, the synthetic approach includes protecting the hydroxyl group (e.g., alcohol) of the acetylene compound (as shown in structure II). In one embodiment, an organic compound, such as dihydropyran, is combined with the acetylene compound. The combination of these compounds can be carried out in the presence of catalyst. The catalyst can be selected from those that are known in the art and commercially available. In one embodiment, p-toluensulfonic acid is used in a catalytic amount. The resulting compound is deprotonated with an organic reagent and condensed with an ester. The organic reagent and the ester can be selected from those that are known in the art and commercially available. In one embodiment, the protected acetylene compound is combined with an organic solvent, such as diethyl ether. To this mixture n-butyl lithium is added and ethyl 2,2-diethoxyacetate is subsequently added to form a substituted acetylene compound. A dithiolene unit is then introduced, for example, by adding a sulfurating agent, and a dithiolene substituted compound having two, five-member rings is formed. The acetal group on the furan ring is deprotected ultimately leading to a substituted six-member pyran ring.

A specific example is discussed in detail in FIG. 1. As illustrated in FIG. 1, the synthetic approach begins with the commercially available acetylene, 2-methyl-3-butyn-2-ol 1 treated with tetrahydropyran (THP) to protect the hydroxyl group (e.g., alcohol). The acetylene 3-methyl-3 tetrahydropyranyloxy-butyne 2-(2-methylbut-3-yn-2-yloxy)tetrahydro-2H-pyran 2 is formed and is then deprotonated with n-butyl lithium and condensed with the ester ethyl 2,2-diethoxyacetate to form the substituted acetylide 1,1-diethoxy-5-methyl-5-(tetrahydro-2H-pyran-2-yloxy)hex-3-yn-2-one 3. A dithiolene unit is then introduced by sulfurating the substituted acetylene 3 with the sulfurating agent 4-phenyl-1,3-dithiolane-2-thione to produce the dithiolene substituted compound 4-(diethoxymethyl)-4-hydroxy-6,6-dimethyl-4,6-dihydro-[1,3]dithiolo[4,5-c]furan-2-thione 4 having a five-member dihydrofuran ring and acetal functionality. The compound 4 is treated with lutidine and trimethylsilyl trifluoromethane sulfonate (TMSOTf) to deprotect the acetal and to form the six-member ring of the compound 6-hydroxy-4,4-dimethyl-2-thioxo-4H-[1,3]dithiolo[4,5-c]pyran-7(6H)-one 6 and 6-hydroxy-4,4-dimethyl-4H-[1,3]dithiolo[4,5-c]pyran-2,7(6H)-dione 8.

NMR and IR spectroscopies and HRMS can be used to determine the structure of compound 4 consistent with the presence of the dithiolene unit, the five-membered dihydrofuran ring and the acetal functionality. Without intending to be bound by any particular theory, it is believed that the presence of the keto-aldehyde functionality can make the compound particularly reactive towards condensation reactions.

Each of the compounds 6 and 8 can be used as a precursor in the synthesis of a substituted pterin compound. The substituted pterin compound can have the general structure represented by structures IIIa and IIIb.

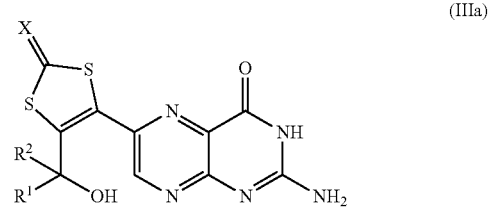

(IIIa)

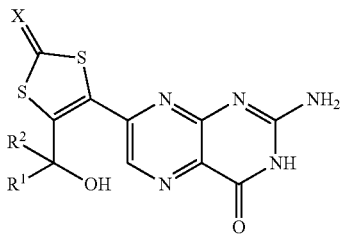

(IIIb)

In structures IIIa and IIIb, X is selected from oxygen or sulfur and, $R^1$ and $R^2$ are each independently selected from hydrogen, substituted and non-substituted, aliphatic and non-aliphatic hydrocarbon, branched and non-branched alkyl, such as $C_1$-$C_6$ alkyl, hydroxy $C_1$-$C_6$ alkyl, alkenyl, alkynyl, cycloalkyl having one or more rings, aryl including benzyl, phenyl, thienyl, indoyl, heteroaryl, phosphate including organic and inorganic, combinations thereof, and derivatives thereof. $R^1$ and $R^2$ may be the same or different. As used herein, the term "aryl" includes an aromatic ring (i.e., a single aromatic ring) or a ring system (i.e., a polycyclic aromatic ring system) in which all ring atoms are carbon. In one embodiment, $R^1$ and $R^2$ are each independently selected from methyl ($CH_3$), hydroxyl ethyl, organic phosphate, and inorganic phosphate. In a preferred embodiment, $R^1$ and $R^2$ are both methyl or hydroxy ethyl or phosphate.

A specific example is discussed in detail in FIG. 2. As illustrated in FIG. 2, the synthetic approach is started with the precursor compound 6 or 8. For example, it is shown in FIG. 2 that the precursor compound 6 can be combined with an organic solvent, such as dichloromethane. The compound 6 in solution can be reacted with o-phenylenediamine to form the open-ring compound 4-(2-hydroxypropan-2-yl)-5-(quinoxalin-2-yl)-1,3-dithiole-2-thione 9. Subsequently, closed-ring compounds can be formed through electrophilic activation with benzyl chloroformate (Cbz-Cl). The compound 11 is a fully oxidized fluorescent quinoxaline derivative. The compound 10 is a reduced quinoxaline with the nitrogen protected with a carboxybenzyl group.

Condensation reactions can be conducted using pyrimidines. The pyrimidines can include protected pyrimidines, such as protected pyrimidine diamine, and unprotected pyrimidines, such as unprotected pyrimidine diamines. In FIG. 2, the precursor compound 6 can be condensed using a partially protected pyrimidine to form the open-ring isomer compounds 12 and 13. Further, in FIG. 2, the precursor compounds 6 and 8 can be condensed using the unprotected pyrimidine 4-hydroxy-2,5,6-triaminopyrimidine sulfate to form the open-ring isomer compounds 14 and 15, and, 16 and 17, respectively. The use of pyrimidines can result in the reaction being completed in a relatively short period of time and yielding significant rates of conversion. In one embodiment, the reaction can be completed in approximately 30 minutes.

It is believed that isomer compounds 14, 15, 16 and 17 which are in a ring-open form can be converted to a ring-closed form. In one embodiment, the synthetic approach may include reacting compound 14 or 15 or 16 or 17 with a protecting agent to protect the nitrogen atoms and cyclize the pyran ring. This can be reduced by a reducing agent to furnish a reduced pterin.

The new substituted pyran and pterin compounds can have various uses and can be suitable for use the fields of medicine, pharmaceuticals, and related fields. It is contemplated that these compounds can be used as therapy for a wide range of medical conditions, such as, but not limited to, cancer, vitamin deficiency, such as, folic acid deficiency, mineral deficiency and molybdenum cofactor deficiency. It is further contemplated that the compounds of the present invention can be administered to a human in therapeutic doses to treat these medical conditions. In one embodiment, the substituted pterin compound is present in a composition that is administered in a therapeutic amount to a patient having a medical condition as described above. Furthermore, it is believed that the new substituted pterin compounds may exhibit antibacterial properties and therefore, may be used as an antibacterial agent.

As used herein, the term "therapeutically effective amount" refers to that amount of any of the new substituted pterin compounds of the present invention incorporated in a pharmaceutical composition which is required to bring about a desired effect. As will be understood by one skilled in the art, a therapeutically effective amount of the new substituted pterin compounds can be administered by any means known in the art including, but not limited to, injection, parenterally, orally, or where appropriate, topically.

EXAMPLES

Materials and Instrumentation

The chemicals used in the following examples were purchased from Aldrich Chemical Company or ACROS Chemical Company and were used without further purification. Ether and dichloromethane were dried using solvent purification system and other solvents were used as received. The radial chromatography was performed with a Chromatotron using silica gel (5-40 μm) purchased from EMD Chemicals. The $^1H$ and $^{13}C$ NMR spectra were recorded on Bruker Avance 400 and Bruker Avance 500 spectrometers operating at 400 MHz and 500 MHz. The IR spectra were recorded using a Nicolet 380 FT spectrophotometer. High resolution mass spectra were recorded on an Agilent 6200 time of flight LC MS system using a nano ESI and APCI-TOF interface.

Synthesis of 3-methyl-3tetrahydropyranyloxy-butyne
2-(2-methylbut-3-yn-2-yloxy)tetrahydro-2H-pyran
(Compound 2)

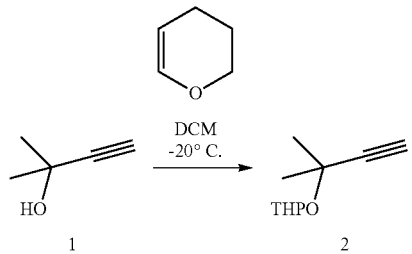

To a cooled (−20° C.) solution of 2-methyl-3-butyn-2-ol 1 (15 g, 0.17 moles) in 150 mL of dry $CH_2Cl_2$, 24.3 g (0.28 mole) dihydropyran was added and a catalytic amount of p-toluensulfonic acid (a few crystals). The progress of the reaction was monitored by thin layer chromatography (TLC) using silica gel as the stationary phase and $CH_2Cl_2$ as the mobile phase, and the spots were detected by concentrated $H_2SO_4$ treatment. The resulting solution was stirred for 80 minutes and washed with a saturated solution of $NaHCO_3$ (3×200 mL). The organic layer was separated and dried over anhydrous $MgSO_4$. The solvent was removed at a reduced pressure and the resulting oil was purified by vacuum distillation to yield the target compound 2. Yield: 27.2 g (0.16 mol; 91%). $^1H$-NMR spectrum in $CDCl_3$ (δ, ppm): 5.06 (m, 1H, THP), 3.95 (m, 2H, THP), 3.50 (m, 2H, THP), 2.43 (s, 1H, alkyne) 1.85 (m, 2H, THP), 1.70 (m, 2H, THP), 1.51 (s, 6H, Me). $^{13}$C NMR spectrum in CDCl$_3$ (δ, ppm): 95.97, 86.25, 86.24, 71.78, 70.72, 63.12, 31.80, 30.47, 29.68, 25.29, 20.29. IR spectra (neat, cm$^{-1}$): 3295, 2941, 2108, 1466, 1380.

Synthesis of 4-phenyl-1,3-dithiolane-2-thione

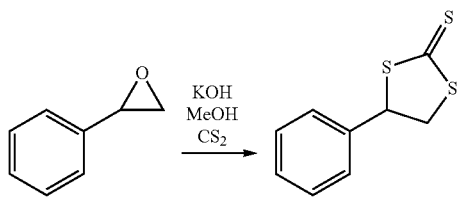 [SMILES: c1ccc(C2CO2)cc1 ; S=C1SCC(c2ccccc2)S1]

To a solution of 21.2 g KOH, dissolved in 160 mL MeOH was added 21 mL (0.33 mmol) CS$_2$, at −20° C. To this solution, 15 mL (0.12 mmol) styrene oxide was added slowly and the reaction mixture was stirred for 6 hours at 0° C. The target compound, 4-phenyl-1,3-dithiolane-2-thione, precipitated as a yellow solid, which was filtered and washed with methanol and water. The solid was dissolved in 50 mL of CH$_2$Cl$_2$, dried with anhydrous MgSO$_4$, filtered, and the organic solvent was removed under reduced pressure to yield a yellow solid. Yield: 13.8 g (0.06 mmol, 52%). IR spectra (neat, cm$^{-1}$): 3027, 1487, 1442, 1045, 878, 690.

Synthesis of 1,1-diethoxy-5-methyl-5-(tetrahydro-2H-pyran-2-yloxy)hex-3-yn-2-one (Compound 3)

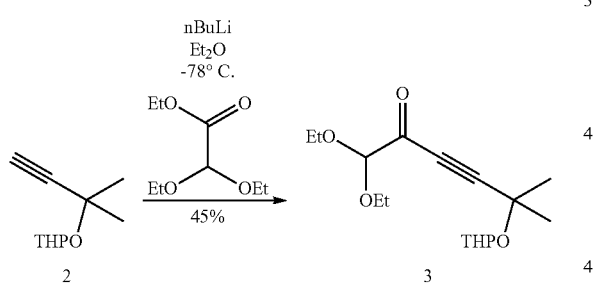

In a 250 mL round bottom flask, 9.5 mL of n-butyl lithium (2.5 M solution in hexane, 23.8 mmol) was added via a syringe to a pre-cooled solution (−78° C.) of 2-(2-methylbut-3-yn-2-yloxy)-tetrahydro-2H-pyran 2 (4.0 g, 23.8 mmol) in 100 mL of Et$_2$O. The resulting solution was stirred for 30 min at −78° C., then ethyl 2,2-diethoxyacetate (4.9 g, 27.7 mmol) was added with a syringe, and the stirring continued for 12 hours. The reaction mixture was poured in an ice-cold saturated aqueous solution of NH$_4$Cl. The aqueous layer was extracted with Et$_2$O (3×50 mL) The organic solvent was separated with a separating funnel and dried with anhydrous MgSO$_4$. The solvent was removed under reduced pressure and the resulting pale yellow oil was purified by radial chromatography (stationary phase silica gel, hexane/AcOEt 90:10) to provide 1,1-diethoxy-5-methyl-5-(tetrahydro-2H-pyran-2-yloxy)hex-3-yn-2-one 3 as a colorless liquid. Yield: 3.2 g (10.7 mmol; 45%). $^1$H-NMR in CDCl$_3$ (δ, ppm): 5.05 (1H, q, J=5.0, 3.5 Hz, THP), 4.73 (1H, s, acetal), 3.92 (1H, m, THP), 3.69 (2H, m, CH$_2$, acetal), 3.62 (2H, m, CH$_2$, acetal), 3.50 (1H, m, THP), 1.82 (1H, m, THP), 1.71 (1H, m, THP), 1.58 (3H, s, CH$_3$), 1.54 (3H, s, CH$_3$), 1.52 (4H, m, THP), 1.25 (6H, t, J=7.0 Hz, CH$_3$, acetal). $^{13}$C-NMR in CDCl$_3$ (δ, ppm): 182.6, 101.1, 97.87, 96.10, 81.25, 70.57, 62.95, 62.64, 62.61, 31.47, 29.45, 28.85, 25.06, 19.92, 14.90 IR (neat, cm$^{-1}$): 2978, 2937, 2872, 2214, 1687, 1074. HR ESIMS$^+$ with acetonitrile as the mobile phase, (m/z): 299.1837 (M$^+$, C$_{16}$H$_{26}$O$_5$, 299.1853), 321.1660 (m/z) ([M+Na]$^+$, C$_{16}$H$_{26}$O$_5$Na, 321.1672).

Synthesis of 4-(diethoxymethyl)-4-hydroxy-6,6-dimethyl-4,6-dihydro-[1,3]dithiolo[4,5-c]furan-2-thione and 2,2-diethoxy-1-(5-(2-(tetrahydro-2H-pyran-2-yloxy)propan-2-yl)-2-thioxo-1,3-dithiol-4-yl)ethanone (Compounds 4 and 5, respectively)

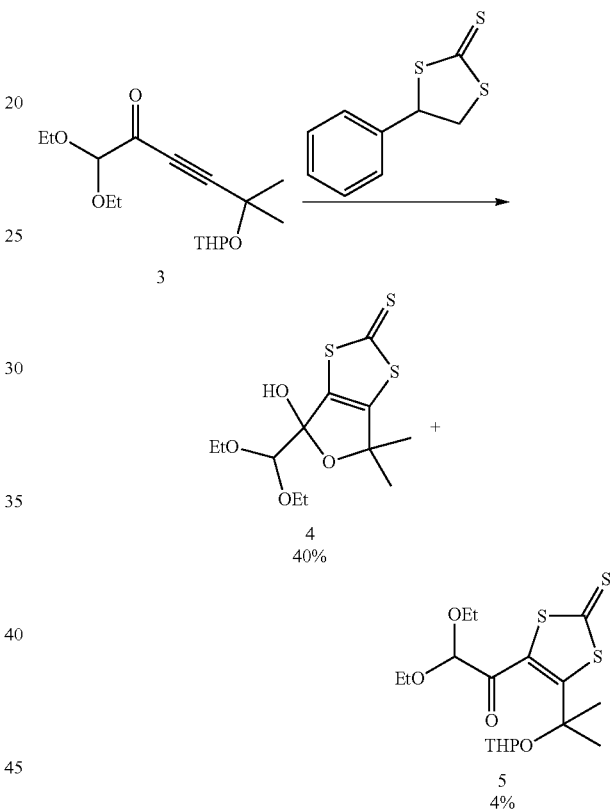

A mixture of 1,1-diethoxy-5-methyl-5-(tetrahydro-2H-pyran-2-yloxy)hex-3-yn-2-one 3 (1.5 g, 5.0 mmol) and 4-phenyl-1,3-dithiolane-thione (5.3 g, 25.0 mmol) was heated under N$_2$ at 130° C. for 1 hour. The reaction was monitored by thin layer chromatography using silica gel as the stationary phase and dichloromethane as the mobile phase. The color of the reaction mixture changed from yellow to dark orange. After completion of the reaction, as evidenced by TLC, the reaction was stopped, cooled, and the target compound 4 was purified by radial chromatography using silica gel as the stationary phase. The target compound 4 eluted as the third fraction with a mixture of dichloromethane and hexanes (60:40). The first band was the excess 4-phenyl-1,3-dithiolane-thione, and the second band yielded 2,2-diethoxy-1-(5-(2-(tetrahydro-2H-pyran-2-yloxy)propan-2-yl)-2-thioxo-1,3-dithiol-4-yl)ethanone 5 which was further converted to 4-(diethoxymethyl)-4-hydroxy-6,6-dimethyl-4,6-dihydro-[1,3]dithiolo[4,5-c]furan-2-thione 4.

2,2-diethoxy-1-(5-(2-(tetrahydro-2H-pyran-2-yloxy)propan-2-yl)-2-thioxo-1,3-dithiol-4-yl)ethanone 5 was isolated as a yellow oil. Yield: 80 mg (0.2 mmol, 4%). $^1$H-NMR spectrum in CDCl$_3$ (δ, ppm): 4.96 (1H, dd; J, 3.7, 4.7 Hz, THP), 4.81 (1H, s, acetal), 3.91 (1H, m, THP), 3.75 (2H, m, CH$_2$, acetal), 3.61 (2H, m, CH$_2$, acetal), 3.50 (1H, m, THP), 1.83 (1H, m, THP), 1.71 (3H, s, CH$_3$), 1.67 (3H, s, CH$_3$), 1.56 (5H, m, THP), 1.23 (6H, dt, J=0.6, 7.0, CH$_3$, acetal). $^{13}$C NMR in CDCl$_3$ (δ, ppm): 211.91, 186.77, 166.07, 130.57, 102.31, 93.94, 80.90, 63.98, 63.88, 62.49, 31.27, 27.38, 25.26, 24.70, 19.49, 15.10, 15.08. IR (neat, cm$^{-1}$): 2974, 2937, 2872, 1703, 1053. HR ESIMS$^+$ (m/z): 407.1005 (M$^+$, C$_{17}$H$_{26}$O$_5$S$_3$, 407.1015).

The third band yielded 4-(diethoxymethyl)-4-hydroxy-6,6-dimethyl-4,6-dihydro-[1,3]dithiolo[4,5-c]furan-2-thione 4 as a dark yellow liquid which solidified after sometime. Yield: 0.642 g (2.0 mmol, 40%). $^1$H-NMR in CDCl$_3$ (δ, ppm): 4.44 (1H, s, acetal), 3.97 (1H, s, —OH), 3.81 (3H, m, acetal), 3.59 (1H, m, CH$_2$, acetal), 1.62 (3H, s, CH$_3$), 1.52 (3H, s, CH$_3$), 1.28 (3H, t; J, 7.0 Hz, CH$_3$, acetal), 1.24 (3H, t; J, 7.0 Hz, CH$_3$, acetal). $^{13}$C NMR in CDCl$_3$ (δ, ppm): 219.08, 150.68, 136.55, 106.34, 103.56, 87.11, 65.87, 65.21, 29.64, 28.53, 15.29, 14.99. IR (neat, cm$^{-1}$): 3419, 2974, 2884, 1057. HR ESIMS$^+$ (m/z): 323.0452 (M$^+$, C$_{12}$H$_{18}$O$_4$S$_3$, 323.0440).

Synthesis of 4-(diethoxymethyl)-4-hydroxy-6,6-dimethyl-4,6-dihydro-[1,3]dithiolo[4,5-c]furan-2-thione (Compound 4)

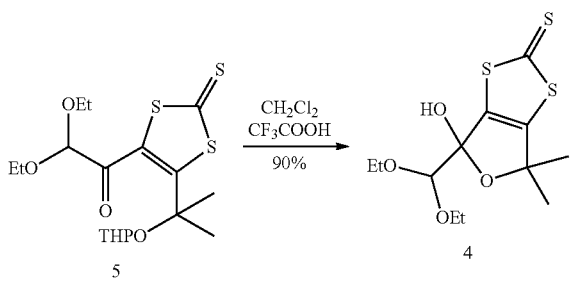

10 mg (0.024 mmol) of 2,2-diethoxy-1-(5-(2-(tetrahydro-2H-pyran-2-yloxy)propan-2-yl)-2-thioxo-1,3-dithiol-4-yl)ethanone 5 was dissolved in 5 mL of CH$_2$Cl$_2$ containing 0.1 mL CF$_3$COOH. The reaction mixture was stirred for 12 hours, washed with 20 mL of saturated solution of NaHCO$_3$ and, the organic layer was separated and dried in vacuum to yield the target compound 4 as a solid material. Yield: 7.2 mg (0.02 mmol, 90%).

Synthesis of 6-hydroxy-4,4-dimethyl-2-thioxo-4H-[1,3]dithiolo[4,5-c]pyran-7(6H)-one and 6-ethoxy-4,4-dimethyl-2-thioxo-4H-[1,3]dithiolo[4,4-c]pyran-7(6H)-one (Compounds 6 and 7, respectively)

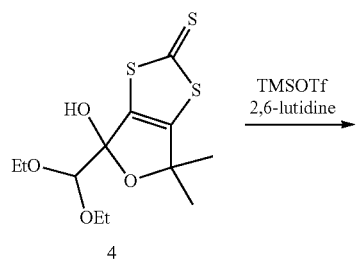

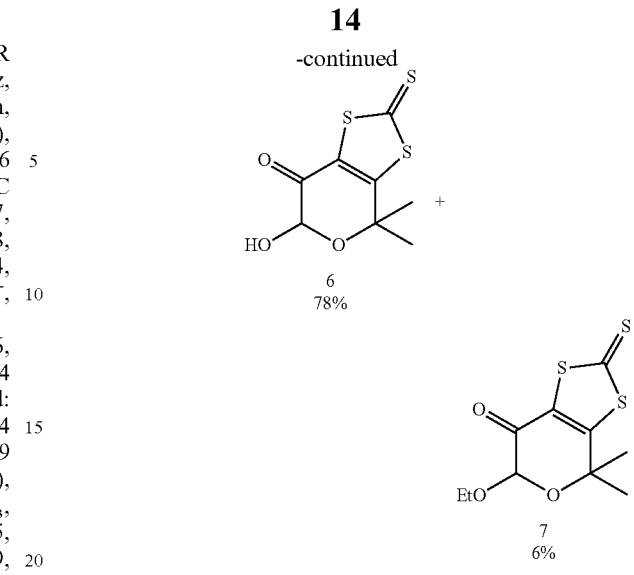

245 mg (0.76 mmol) of 4-(diethoxymethyl)-4-hydroxy-6,6-dimethyl-4,6-dihydro-[1,3]dithiolo[4,5-c]furan-2-thione 4 was dissolved in 2.5 mL of dry CH$_2$Cl$_2$ under nitrogen atmosphere inside a Nexus One inert atmosphere box. To this solution, 758 μl (6.57 mmol) of 2,6-lutidine was added followed by addition of 843 μl (4.65 mmol) of trimethylsilyl trifluoromethanesulfonate. The mixture was stirred for 17 hours at room temperature and 3 mL water, 3 mL acetone, and 1 drop formic acid were added sequentially. The mixture was refluxed for 1 hour. The organic material was extracted with CH$_2$Cl$_2$ and washed with a saturated solution of NaHCO$_3$. The organic layer was separated and dried over anhydrous MgSO$_4$. The solvent was removed by vacuum and the resulting solid was purified by radial chromatography using CH$_2$Cl$_2$ as the mobile phase. The first yellow fraction was the 6-ethoxy-4,4-dimethyl-2-thioxo-4H-[1,3]dithiolo[4,4-c]pyran-7(6H)-one 7 isolated as a yellow oil. Yield: 12 mg (0.05 mmol, 6%). $^1$H NMR in CDCl$_3$ (δ, ppm): 5.05 (1H, s, acetal), 3.95 (1H, m, CH$_2$, acetal), 3.68 (m, 1H, CH$_2$, acetal), 1.78 (3H, s, CH$_3$), 1.60 (3H, s, CH$_3$), 1.26 (3H, t, J=7.1 Hz, CH$_3$, acetal). $^{13}$C NMR in CDCl$_3$ (δ, ppm): 208.78, 179.10, 167.34, 133.35, 98.23, 75.50, 65.57, 31.90, 31.23, 15.24. IR (neat, cm$^{-1}$): 2978, 2925, 2888, 2691, 1041. HR APCIMS$^+$ (m/z): 277.0012 (M$^+$, C$_{10}$H$_{12}$O$_3$S$_3$, 277.0021).

The second fraction was 6-hydroxy-4,4-dimethyl-2-thioxo-4H-[1,3]dithiolo[4,5-c]pyran-7(6H)-one 6 isolated as a dark yellow liquid that solidified. Yield: 146.3 mg (0.59 mmol, 78%). $^1$H-NMR in CDCl$_3$ (δ, ppm): 5.50 (1H, d; J, 6.0 Hz hemiacetal), 3.54 (1H, d; J, 6.0 Hz, OH,), 1.75 (3H, s, CH$_3$), 1.69 (3H, s, CH$_3$). $^{13}$C NMR in CDCl$_3$ (δ, ppm): 207.93, 181.1, 167.6, 132.31, 91.28, 75.71, 31.37, 28.51. IR (neat, cm$^{-1}$): 3366, 2978, 2929, 2869, 1679, 1078, 1017. HR APCIMS$^+$ (m/z): 248.9700 (M$^+$, C$_8$H$_8$O$_3$S$_3$, 248.9708).

Synthesis of 6-hydroxy-4,4-dimethyl-4H-[1,3]dithiolo[4,5-c]pyran-2,7(6H)-dione (Compound 8)

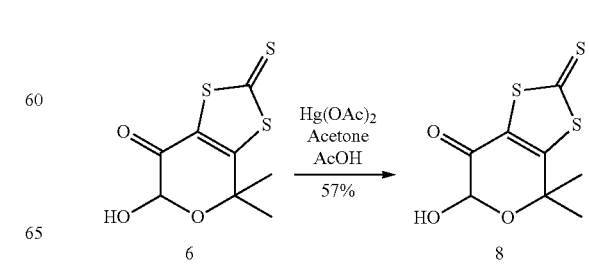

13 mg (0.05 mmol) of 6-hydroxy-4,4-dimethyl-2-thioxo-4H-[1,3]dithiolo[4,5-c]pyran-7(6H)-one 6 was dissolved in acetone (5 mL) and added to a solution of Hg(OAc)$_2$ (50 mg, 0.15 mmol) in 1 ml of acetic acid. The color of the reaction mixture changed very fast from yellow to white. The solution was stirred for 10 minutes and then 20 mL of water was added. The resulting mixture was extracted with CH$_2$Cl$_2$ (3×5 mL). The organic layer was separated and then was washed with saturated aqueous NaHCO$_3$ (10 mL) The organic layer was separated again and the aqueous layer was re-extracted again with CH$_2$Cl$_2$ (2×5 mL). The organic layers were combined and evaporated to get 6-hydroxy-4,4-dimethyl-4H-[1,3]dithiolo[4,5-c]pyran-2,7(6H)-dione 8 as a pale beige oil. Yield: 7 mg (0.03 mmol, 57%). $^1$H NMR in CDCl$_3$ (δ, ppm): 5.51 (1H, s, hemiacetal), 1.74 (3H, s, CH$_3$), 1.68 (3H, s, CH$_3$). $^{13}$C NMR in CDCl$_3$ (δ, ppm): 187.09, 181.81, 159.93, 124.38, 91.15, 76.16, 31.47, 28.27. IR (neat, cm$^{-1}$): 3419, 2978, 2929, 2864, 1670, 1625, 1548.

Synthesis of 4-(2-hydroxypropan-2-yl)-5-(quinoxalin-2-yl)-1,3-dithiole-2-thione (Compound 9)

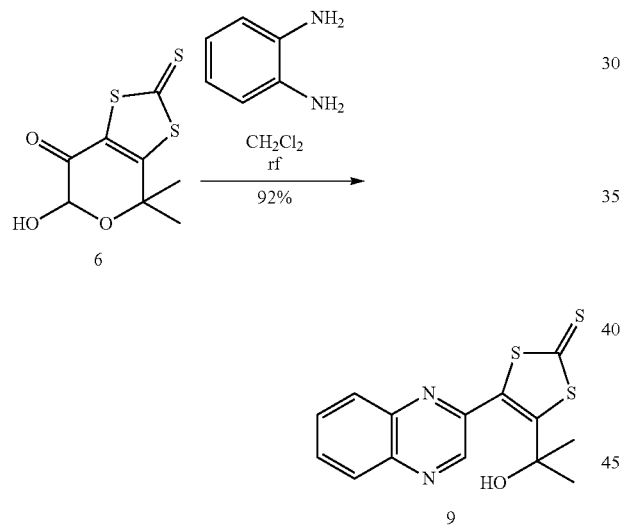

To a solution of 6-hydroxy-4,4-dimethyl-2-thioxo-4H-[1,3]dithiolo[4,5-c]pyran-7(6H)-one 6 (101.0 mg, 0.41 mmol) in CH$_2$Cl$_2$ (15 mL), 136.6 mg (1.26 mmol) of o-phenylenediamine was added, the resulting solution was refluxed for 1 hour. The reaction mixture was cooled to room temperature and the solvent was evaporated under reduced pressure. The residue was purified by radial chromatography using CH$_2$Cl$_2$ as a mobile phase that yielded 4-(2-hydroxypropan-2-yl)-5-(quinoxalin-2-yl)-1,3-dithiole-2-thione 9 as a yellow-orange solid (119.6 mg, 0.37 mmol, 92.0%). $^1$H NMR in CDCl$_3$ (δ, ppm): 9.01 (1H, s), 8.18 (1H, m, ArH), 8.07 (1H, m, ArH), 7.89 (2H, m, ArH), 1.59 (6H, s, CH$_3$); $^{13}$C NMR in CDCl$_3$ (δ, ppm): 207.8, 158.0, 145.1, 144.3, 141.9, 140.0, 133.81, 132.3, 131.9, 129.8, 128.7, 72.3, 31.0; IR (neat, cm$^{-1}$): 3199, 3007, 2962, 2917, 1531, 1045, 759, 571, 457; HR APCIMS$^+$ (m/z): 321.0179 (M$^+$, C$_{14}$H$_{12}$N$_2$OS$_3$, 321.0185).

Formation of the Pyran Ring in Compound 9

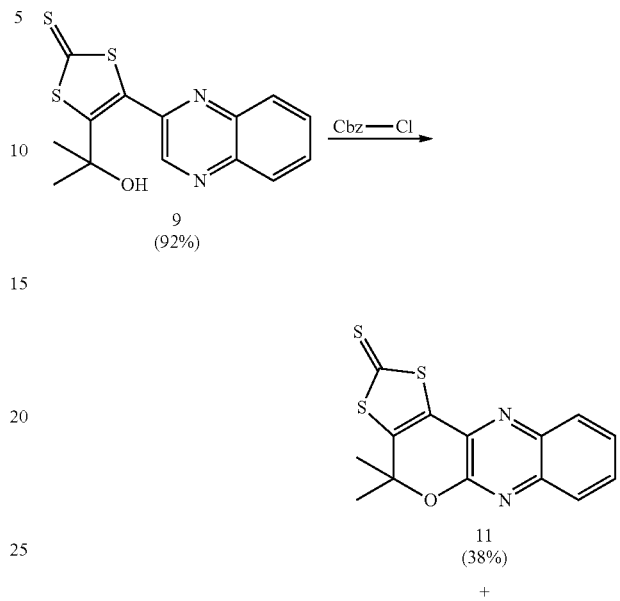

To compound 9 (34.6 mg, 0.11 mmol in 2 ml dichloromethane), 8 ml of benzylchloroformate (56 mmol) was added. The reaction mixture was stirred at room temperature for a short time, the solution was evaporated to dryness in vacuum in a span of 48 h. The residue was purified by preparative TLC (silica gel, stationary phase; dichloromethane, mobile phase). The first fraction was collected to be compound 10 in ~16% yield, and second band yielded compound 11 in 38% yield. Characterization data for compound 10, $^1$H-NMR in CDCl$_3$ (δ, ppm): 8.17 (1H, dd; J, 1.2, 8.5 Hz, ArH), 7.45 (1H, dd; J, 1.6, 7.5 Hz, ArH), 7.38 (m, ArH), 7.13 (1H, td; J, 1.4, 7.78 Hz, ArH), 6.16 (1H, s; H-5a), 5.32 (2H, d; J, 2.8 Hz, COHCHPh), 1.48 (3H, s., CH$_3$), 1.43 (3H, s, CH$_3$). Characterization data for compound 11, $^1$H-NMR s in CDCl$_3$ (δ, ppm): 7.96 (1H, d; J, 1.4, 8.0 Hz), 7.83 (1H, d; J, 1.4, 8.0 Hz), 7.68 (1H, td; J, 8.0, 1.4 Hz), 7.61 (1H, td; J, 8.0, 1.4 Hz), 1.84 (6H, s, CH$_3$). $^{13}$C-NMR in CDCl$_3$ (δ, ppm): 209.7; 152.6; 149.4; 141.2; 139.6; 133.3; 133.1; 130.8; 128.7; 128.2; 127.5; 80.9; 30.1. IR (neat, cm$^{-1}$): 1573, 1492, 1463, 1409, 1365. APCIMS$^+$ (m/z): 318.85 (C$_{14}$H$_{11}$N$_2$OS$_3$, 319.00). UV-vis in acetonitrile (λ$_{max}$, nm (ε, M$^{-1}$ cm$^{-1}$)): 227 (17785), 257 (12623), 391 (16664), 410 (20682).

17

Synthesis of a pterin dithiolene compounds, 7-(5-(2-hydroxypropan-2-yl)-2-thioxo-1,3-dithiol-4-yl)-2-morpholinopteridin-4(3H)-one and 7-(5-(2-hydroxypropan-2-yl)-2-thioxo-1,3-dithiol-4-yl)-2-morpholinopteridin-4(3H)-one (Compounds 12 and 13, respectively)

18

Synthesis of 2-amino-6-(5-(2-hydroxypropan-2-yl)-2-thioxo-1,3-dithiol-4-yl)pteridin-4(3H)-one and 2-amino-7-(5-(2-hydroxypropan-2-yl)-2-thioxo-1,3-dithiol-4-yl)pteridin-4(3H)-one (Compounds 14 and 15, respectively)

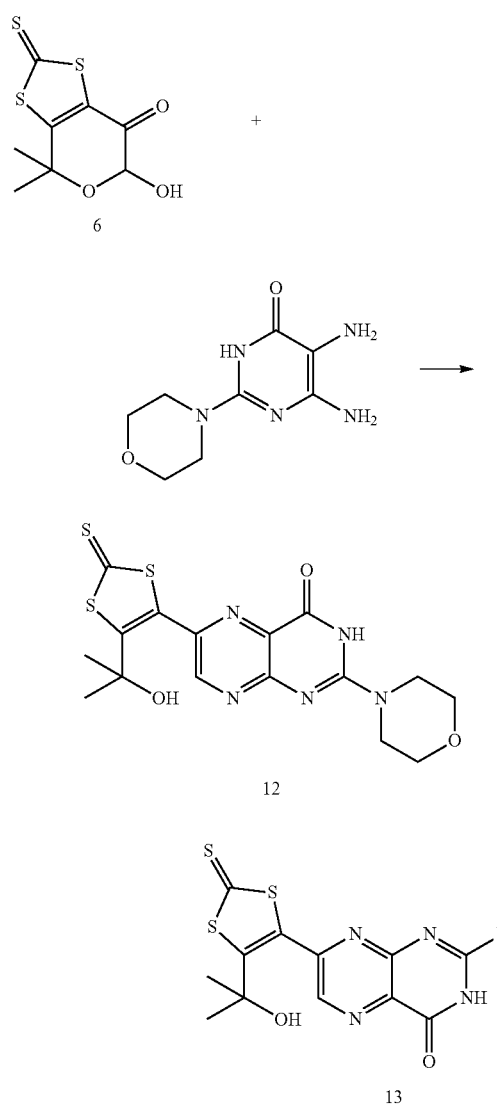

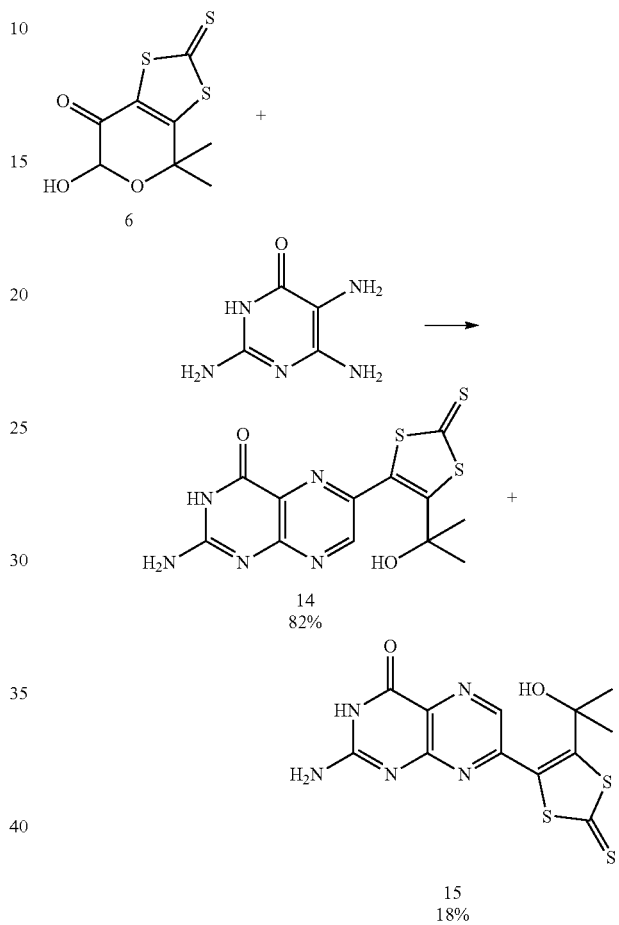

4.5 mg of compound 6 (0.018 mmol) dissolved in DMSO was reacted with morpholine protected 5,6 diaminopyrimidine in a NMR tube for 40 mins maintaining the temperature in a boiling water bath. The reaction mixture was followed by NMR spectroscopy, transferred into a flask containing a small amount of water. It was then extracted with a small amount of dichloromethane, the organic solvent was removed in vacuum. Yield, 5.5 mg (0.013 mmol, 72%) of compounds 12 and 13. $^1$H-NMR in DMSO (δ, ppm): 12, 8.92 (1H, s, H—C7), 1.41 (6H, s, CH$_3$); 13, 8.66 (1H, s, H—C$_6$), 1.43 (6H, s, CH$_3$). HR ESI MS$^+$ (m/z): 424.0581 (M$^+$, C$_{16}$H$_{19}$N$_5$O$_3$S$_3$, 424.0566).

45.0 mg 4-hydroxy-2,5,6-triaminopyrimidine sulfate (0.20 mmol) was suspended in 5 mL of water (pH, 2.3) and solid sodium bicarbonate was added slowly to adjust the pH of the solution to 4.5. To this solution, solid sodium bisulfite was added slowly and the pH was adjusted to 5.9. To this solution, a solution of 6-hydroxy-4,4-dimethyl-2-thioxo-4H-[1,3]dithiolo[4,5-c]pyran-7(6H)-one 6 (50 mg, 0.20 mmol, in 5 mL ethanol) was added drop wise, and the reaction mixture was stirred at room temperature for 25 hours. The resulting slurry was centrifuged. The solid was washed with water followed by ethanol, and dried in vacuum to give yellow colored fine powder. The ratio of the two isomers, 14:15 was ~82:18, as evidenced by $^1$H NMR spectrum. Yield: 30 mg (0.085 mmol, 42%). $^1$H-NMR in DMSO (δ, ppm): 14, 8.89 (1H, s, H—C7), 1.44 (6H, s, CH$_3$); 15, 8.60 (1H, s, H—C6), 1.46 (6H, s, CH$_3$); $^{13}$C NMR in DMSO (δ, ppm): 211.45, 161.60, 157.82, 157.62, 155.89, 151.32, 138.82, 133.71, 128.91, 73.75, 31.9. IR (neat, cm$^{-1}$): 3346, 3364, 3129, 3966, 2921, 2827, 1699, 1536, 1045, 624, 530, 440. HR ESI MS$^+$ (m/z): 354.0122 (M$^+$, C$_{12}$H$_{11}$N$_5$O$_2$S$_3$, 354.0148).

Synthesis of 2-amino-6-(5-(2-hydroxypropan-2-yl)-2-oxo-1,3-dithiol-4-yl)pteridin-4(3H)-one and 2-amino-7-(5-(2-hydroxypropan-2-yl)-2-oxo-1,3-dithiol-4-yl)pteridin-4(3H)-one (Compounds 16 and 17, respectively)

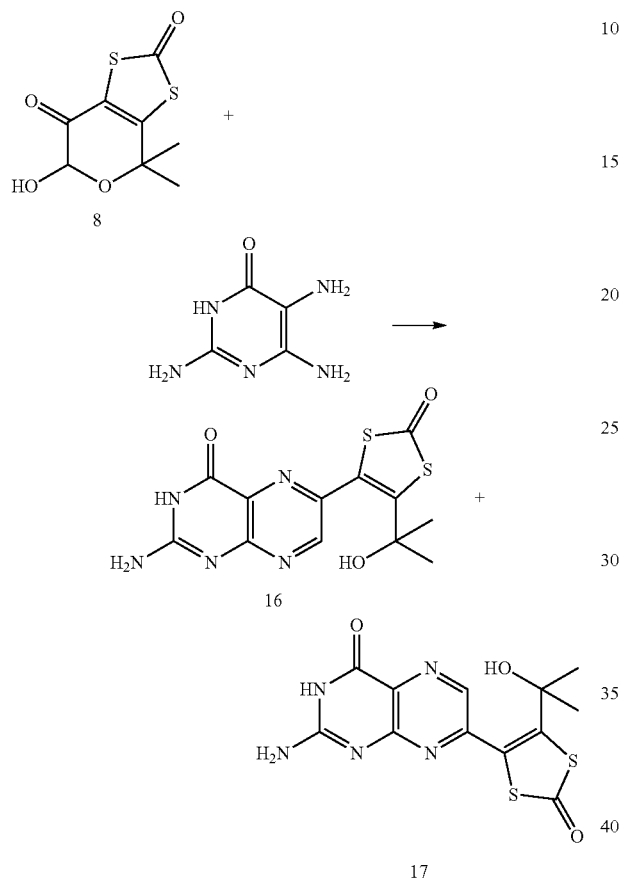

A small amount of 6-hydroxy-4,4-dimethyl-4H-[1,3]dithiolo[4,5-c]pyran-2,7(6H)-dione, 8 was dissolved in DMSO-$d_6$. Then, 4-hydroxy-2,5,6-triaminopyrimidine sulfate and solid sodium bisulfite were suspended in this solution. The color of the reaction mixture changed from colorless to green and then yellow. The mixture was heated on a water bath for 15 min. The mixture was analyzed by NMR.
$^1$H-NMR in DMSO (δ, ppm): 16, 8.84 (1H, s, H—C7), 1.39 (6H, s, $CH_3$); 17, 8.55 (1H, s, H—C6), 1.43 (6H, s, $CH_3$).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A compound of a structure selected from the group consisting of:

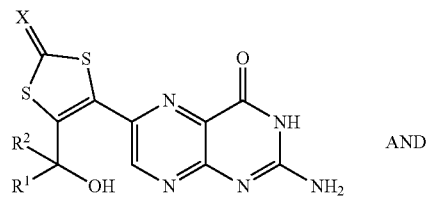

IIIa

AND

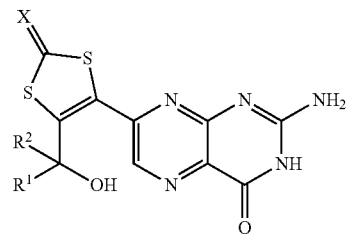

IIIb wherein X is selected from the group consisting of oxygen and sulfur and, $R^1$ and $R^2$ are each independently unsubstituted $C_1$-$C_6$ alkyl.

2. A method of preparing a compound having a structure selected from the group consisting of:

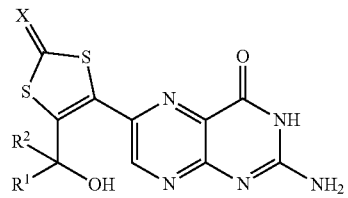

IIIa

AND

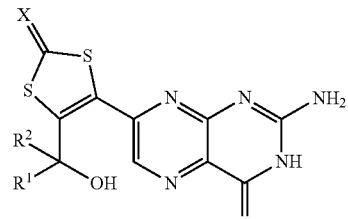

IIIb wherein X is selected from the group consisting of oxygen and sulfur and, $R^1$ and $R^2$ are each independently unsubstituted $C_1$-$C_6$ alkyl,
comprising:
starting with a precursor compound having a structure I:

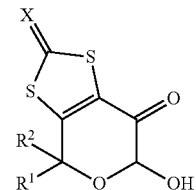

I wherein X is selected from the group consisting of oxygen and sulfur and, $R^1$ and $R^2$ are each independently unsubstituted $C_1$-$C_6$ alkyl; and combining the precursor compound having the structure I with 4-hydroxy-2,5,6-triaminopyrimidine sulfate in a condensation reaction to form the compound having a structure selected from the group consisting of IIIa and IIIb.

3. A therapeutic composition comprising the compound of claim 1.

4. A method of treating molybdenum co-factor deficiency comprising administering a therapeutically effective amount of the compound of claim 1.

* * * * *